US008569356B2

(12) United States Patent
Ostrov et al.

(10) Patent No.: US 8,569,356 B2
(45) Date of Patent: Oct. 29, 2013

(54) CYCLIN DEPENDENT KINASE INHIBITORS

(75) Inventors: David A. Ostrov, Gainesville, FL (US);
Brian K. Law, Gainesville, FL (US);
Patrick Corsino, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 895 days.

(21) Appl. No.: 12/084,184

(22) PCT Filed: Oct. 25, 2006

(86) PCT No.: PCT/US2006/041605
§ 371 (c)(1),
(2), (4) Date: Sep. 29, 2009

(87) PCT Pub. No.: WO2007/050673
PCT Pub. Date: May 3, 2007

(65) Prior Publication Data
US 2010/0035940 A1 Feb. 11, 2010

Related U.S. Application Data

(60) Provisional application No. 60/730,251, filed on Oct. 25, 2005.

(51) Int. Cl.
| A01N 43/18 | (2006.01) |
| A01N 33/02 | (2006.01) |
| A01N 43/06 | (2006.01) |
| A61K 31/38 | (2006.01) |
| A61K 31/135 | (2006.01) |
| C07D 335/04 | (2006.01) |
| C07D 335/06 | (2006.01) |
| C07D 495/00 | (2006.01) |
| C07D 333/08 | (2006.01) |
| C07C 211/00 | (2006.01) |

(52) U.S. Cl.
USPC ........... 514/432; 514/438; 514/646; 514/657; 549/23; 549/80; 564/429; 564/441

(58) Field of Classification Search
USPC .............. 514/432, 438, 646, 657; 549/23, 80; 564/429, 441
See application file for complete search history.

(56) References Cited

U.S. PATENT DOCUMENTS

| 5,827,900 A * | 10/1998 | Levy et al. ............... 514/762 |
| 2005/0043262 A1 | 2/2005 | Weiss |
| 2005/0107339 A1 | 5/2005 | Muller et al. |
| 2005/0124610 A1 | 6/2005 | Lin et al. |

FOREIGN PATENT DOCUMENTS

| WO | WO 9966915 A2 * 12/1999 |
| WO | WO 03087066 A1 * 10/2003 |

OTHER PUBLICATIONS

Park et. al., Clinical Cancer Research, 2004, American Association for Cancer Research, vol. 10, issue 15, pp. 5271-5281.*
http://www.cancer.gov/cancertopics/types/alphalist/y.*
Bailar et. al., The New England Journal of Medicine, 1997, Massachusetts Medical Society, vol. 336, issue 22, pp. 1569-1574.*
Giese et. al., Journal of Cancer Research and Clinical Oncology, 2001, Springer-Verlag, vol. 127, pp. 217-225.*
Martinet et. al., Journal of the National Cancer Institute, 2000, National Cancer Institute, vol. 92, pp. 931-936.*
Liu et. al., Clinical Cancer Research, 2004, American Association for Cancer Research, vol. 10, pp. 924-928.*
Stadler et. al., Journal of Clinical Oncology, 2000, American Society for Clinical Oncology, vol. 18, No. 2, pp. 371-375.*
http://www.thefreedictionary.com/prevent.*
Surh, Nature Rev. Cancer, 2003, Nature Publishing Group, vol. 3, pp. 768-780.*
Cuzick et. al., The Lancet, 2003, The Lancet Publishing Group, vol. 361, pp. 296-300.*
Nahum et. al., Oncogene, 2001, Nature Publishing Group, vol. 20, pp. 3428-3436.*
Magarian et. al., Journal of Pharmaceutical Sciences, 1969, American Pharmaceutical Association, vol. 58, issue 9, pp. 1166-1167.*
Chen et. al., Molecular and Cellular Biology, 1996, American Society for Microbiology, vol. 16, No. 9, pp. 4673-4682.*
PCT International Search Report and Written Opinion dated Sep. 5, 2007, in corresponding PCT Patent Application No. PCT/US06/41605.

* cited by examiner

Primary Examiner — Sreeni Padmanabhan
Assistant Examiner — Sarah Pihonak
(74) Attorney, Agent, or Firm — Edwards Wildman Palmer LLP; Jeffrey D. Hsi; Mark D. Russett

(57) ABSTRACT

The invention relates to cyclin dependent kinase inhibitor compounds and methods of identifying and using them. The invention further relates to pharmaceutical compositions for treating cell proliferative disorders, especially cancer.

8 Claims, 10 Drawing Sheets

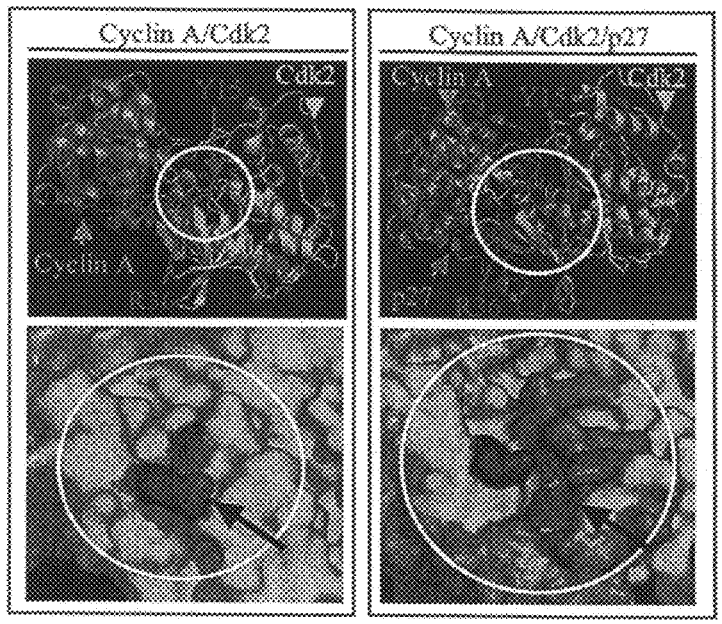

Figure 1. Crystal structures of Cyclin A/Cdk2 and Cyclin A/Cdk2/p27 complexes reveal a target for small molecule binding. Cyclin A/Cdk2 complexes are shown as ribbon diagrams (top left) and as space-filled models (bottom left). The Cyclin A and Cdk2 subunits and the Tyr15 (Y15) and Arg36 (R36) residues of Cdk2 are denoted by arrows. Note that Y15 and R36 are tightly packed together and the Y15 sidechain is inserted into the core of the protein. In contrast, note that in the Cyclin A/Cdk2/p27 structure (right panels) the Y15 and R36 residues of Cdk2 are separated by a cleft. p27 is shown in light gray in the lower right panel. This cleft is specific to the Cyclin A/Cdk2/p27 complex and will be targeted in *in silico* molecular docking studies.

Figure 1

CYCLIN DEPENDENT KINASE INHIBITORS

CROSS-REFERENCE TO RELATED APPLICATIONS

This application is the 35 U.S.C. §371 national stage of PCT application PCT/US2006/041605, filed Oct. 25, 2006, which claims priority to U.S. Provisional Patent Application No. 60/730,251, filed Oct. 25, 2005; the contents of these applications are hereby incorporated by reference.

STATEMENT OF RIGHTS TO INVENTIONS MADE UNDER FEDERALLY SPONSORED RESEARCH

This invention was made with government support under Grant No. R01-CA93651 awarded by the National Institutes of Health/NCI. The government has certain rights in the invention.

BACKGROUND OF THE INVENTION

Cancer is a disease of uncontrolled cell division. Tumor cells achieve this state by overriding signals from growth inhibitory factors such as Transforming Growth Factor-β (TGFβ) [2-4] and acquiring constitutive activation of mitogenic signaling pathways such as the mammalian Target of Rapamycin (mTOR)/p70$^{s6k}$ pathway [5,6]. It has been demonstrated that activation of the TGFβ signaling pathway and simultaneous inactivation of mTOR signaling by the TOR inhibitor rapamycin synergize to inhibit the proliferation of human mammary carcinoma cells [7,8]. TGFβ+rapamycin-induced inhibition of cancer cell proliferation is caused by a dramatic increase in the association of the cyclin-dependent kinase inhibitor p27$^{kip1}$ with the cyclin-dependent kinase Cdk2.

Despite the potent cytostatic action of TGFβ+rapamycin treatment on cancer cells in vitro, it is unlikely that this therapeutic strategy can be directly employed clinically. In addition to inhibiting cell proliferation, TGFβ also exhibits pro-tumorigenic [9-11] and pro-fibrotic [12] effects, and it would be difficult to deliver to cancers. Rapamycin derivatives RAD001 and CCI-779 are currently in clinical trials against several types of human tumors, and based on current data, have the potential to prove useful as cancer therapeutics. A drawback of using rapamycin as a cancer therapeutic is that it acts as an immunosuppressant by inhibiting the proliferation of B-cells and T-cells in addition to inhibiting cancer cell division.

SUMMARY OF THE INVENTION

In one aspect, the invention provides a method of treating a subject suffering from or susceptible to a cell proliferative disorder comprising administering to subject in need thereof a therapeutically effective amount of a compound capable of stabilizing an inactive conformation of a cyclin-dependent kinase and/or a complex of a cyclin-dependent kinase and a cyclin. In one embodiment, the compound is capable of binding to or interacting with a binding pocket defined by structure coordinates of Cdk2 amino acid residues 14-19, and 30-37, and p27 amino acids 67, 78-81, and 86-92. In another embodiment, the compound is capable of binding to or interacting with a binding pocket defined by structure coordinates of 13-18, 20, 28, 31, 33, 51, 80-89, 131-136, and 145.

In one aspect, the invention provides a method of treating a subject suffering from or susceptible to a cell proliferative disorder. The method includes administering to a subject in need thereof a therapeutically effective amount of a cyclin-dependent kinase downregulator compound.

In another aspect, the invention provides a method of treating a subject suffering from or susceptible to a cell proliferative disorder. The method includes administering to a subject in need thereof a therapeutically effective amount of a compound capable of stabilizing the interaction of a cyclin-dependent kinase and a cdk inhibitor such as p27 (or related inhibitors such as p21 or p57), e.g., by binding to a binding pocket ("Pocket #1") of a complex of a cyclin dependent kinase with the inhibitor. In certain embodiment, the compound is a compound disclosed herein, e.g., a compound of Table 1.

In another embodiment, the invention provides a method of treating a subject suffering from or susceptible to a cell proliferative disorder. The method includes administering to a subject in need thereof a therapeutically effective amount of a cyclin-dependent kinase downregulator compound. In certain embodiments, the cyclin-dependent kinase downregulator compound is selected from

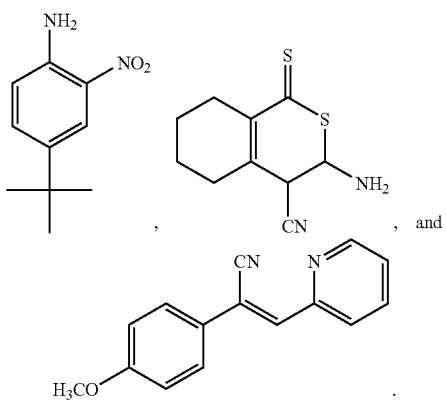

In another aspect, the invention provides a method of treating a subject suffering from or susceptible to a cell proliferative disorder, including cancer. The method includes administering to a subject in need thereof a therapeutically effective amount of a compound capable of binding to a complex of a cyclin-dependent kinase (such as Cdk2) and a cyclin (such as cyclin A), e.g., by binding to a pocket ("Pocket #2") overlapping a p27 binding site in a Cyclin/Cdk complex (e.g., a Cyclin A/Cdk2 complex).

In another aspect, the invention provides a method of treating a subject suffering from or susceptible to cancer, comprising administering to the subject an effective amount of a compound capable of downregulating cdk expression in a cell, such that the subject is treated.

In another aspect, the invention provides a method for identifying a compound that modulates the interaction of a cyclin dependent kinase with p27, the method comprising obtaining a crystal structure of a cyclin dependent kinase or obtaining information relating to the crystal structure of a cyclin dependent kinase, in the presence and/or absence of p27, and modeling a test compound into or on the p27 binding site of the crystal structure to determine whether the compound modulates the interaction of a cyclin dependent kinase with p27. In certain embodiments, the step of modeling comprises modeling or determining the ability of the compound to bind to or associate with a binding pocket defined by structure coordinates of Cdk2 amino acid residues 14-19, and 30-37, and p27 amino acids 67, 78-81, and 86-92.

Yet another aspect of the invention is a method for identifying a compound that inhibits cell proliferation. The method includes contacting a cyclin/cyclin-dependent kinase complex with a test compound in the presence of a cdk inhibitor such as p27 (or related inhibitors such as p21 or p57), and evaluating the ability of the test compound to stabilize the interaction of the cyclin/cyclin-dependent kinase complex and the inhibitor, wherein an increase in the stability of the interaction of the cyclin/cyclin-dependent kinase complex and the inhibitor relative to a reference value is an indication that the test compound inhibits cell proliferation.

Yet another aspect of the invention is a method for identifying a compound that modulates the activity of a cyclin dependent kinase, the method comprising using the atomic coordinates of Cdk2 amino acid residues 14-19 and 30-37, and p27 amino acids 67, 78-81, and 86-92, to generate a three-dimensional structure of a molecule comprising a Cdk2 binding pocket, and employing the three-dimensional structure to identify a compound that modulates the activity of a cyclin dependent kinase.

Still another aspect of the invention is a method for identifying a compound that modulates the activity of a cyclin dependent kinase, the method comprising using the atomic coordinates of 13-18, 20, 28, 31, 33, 51, 80-89, 131-136, 145, to generate a three-dimensional structure of a molecule comprising a Cdk2 binding pocket, and employing the three-dimensional structure to identify a compound that modulates the activity of a cyclin dependent kinase.

In another aspect, the invention provides a polypeptide including a cyclin binding region and a p27 binding region of a cyclin-dependent kinase.

In another aspect, the invention provides a method for inhibiting cell proliferation comprising contacting cells with a compound capable of downregulating the expression of a cyclin dependent kinase in the cells, under conditions such that expression of the cyclin dependent kinase is down-regulated.

In still another aspect, the invention provides A method for identifying a compound capable of modulating the stability of a cyclin dependent kinase-p27 complex, the method comprising contacting a cyclin dependent kinase with a test compound in the presence of p27, and evaluating the stability of a cyclin dependent kinase-p27 complex, wherein a change in the stability of the complex relative to a reference value is an indication that the test compound modulates the stability of the complex.

In another aspect, the invention provides a method for identifying a compound that inhibits cell proliferation. The method includes contacting: 1) a complex of a) a cyclin and b) a polypeptide including a cyclin binding region and a p27 binding pocket of a cyclin-dependent kinase with 2) a test compound in the presence of 3) p27; and evaluating the ability of the test compound to stabilize the interaction of the complex polypeptide and p27, wherein an increase in the stability of the interaction of the complex and p27 relative to a reference value is an indication that the test compound inhibits cell proliferation.

In another aspect, the invention provides a method for downregulating expression of a cyclin dependent kinase in a cell, the method comprising contacting the cell with an effective amount of a compound capable of downregulating expression of a cyclin dependent kinase, such that expression of a cyclin dependent kinase is down-regulated.

In another aspect, the invention provides a method for stabilizing an interaction of a cyclin dependent kinase with p27, the method comprising contacting the cyclin dependent kinase, in the presence of p27, with a compound capable of stabilizing an interaction of a cyclin dependent kinase with p27, such that an interaction of a cyclin dependent kinase with p27 is stabilized.

In another aspect, the invention provides a packaged composition including a therapeutically effective amount of a cyclic-dependent kinase downregulator compound and a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In one aspect, the invention provides a kit for treating a cell proliferative disorder in a subject is provided and includes a compound of formula I, a pharmaceutically acceptable esters, salts, and prodrugs thereof and instructions for use. In further aspects, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In certain embodiments, the invention provides: a kit for treating a cell proliferative disorder in a subject, the kit comprising a compound capable of stabilizing an interaction of a cyclin dependent kinase with p27, pharmaceutically acceptable esters, salts, and prodrugs thereof, and instructions for use; in certain embodiments, the compound is represented by any of the structures of Table 1 or Table 2, or a pharmaceutically acceptable salt thereof; in certain embodiments, the compound is selected from the group consisting of 4-t-butyl-2-nitro-aniline, 3-amino-1-sulfanylidene-5,6,7,8-tetrahydroisothiochromene-4-carbonitrile, and 2-(4-methoxyphenyl)-3-pyridin-2-yl-prop-2-enenitrile.

In another aspect, the invention relates to a three-dimensional structure of a cyclin A/Cdk2/p27 complex. The invention provides the key structural features of the cyclin A/Cdk2/p27 complex, particularly the shape of small-molecule binding pockets near the p27 binding site of Cdk2.

Thus, the present invention provides molecules or molecular complexes that comprise either one or both of these binding pockets or homologues of either binding pocket that have similar three-dimensional shapes.

The invention also provides a pharmaceutical compositions of the compounds described herein, e.g., the compounds of Table 1, comprising a compound capable of stabilizing an interaction of a cyclin dependent kinase with p27, or a pharmaceutically acceptable ester, salt, or prodrug thereof, together with a pharmaceutically acceptable carrier.

In another aspect, the invention provides a machine readable storage medium which comprises the structural coordinates of a binding pocket defined by structure coordinates of Cdk2 amino acid residues 14-19, and 30-37, and p27 amino acids 67, 78-81, and 86-92, or a homologous binding pocket.

In another aspect, the invention provides a machine readable storage medium which comprises the structural coordinates of a binding pocket defined by structure coordinates of Cdk2 amino acid residues 13-18, 20, 28, 31, 33, 51, 80-89, 131-136, and 145, or a homologous binding pocket.

In another aspect, the invention provides a computer for producing a three-dimensional representation of a molecule or molecular complex, wherein said molecule or molecular complex comprises a binding pocket defined by structure coordinates of Cdk2 amino acid residues 14-19, and 30-37, and p27 amino acids 67, 78 81, and 86-92; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes (i) a machine-readable data storage medium comprising a data storage material encoded with machine-readable data, wherein said data comprises the structure coordinates of Cdk2 amino acid residues 14-19 and 30-37, and p27 amino acids 67, 78-81, and 86-92; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

In another aspect, the invention provides a computer for producing a three-dimensional representation of a molecule or molecular complex, wherein said molecule or molecular complex comprises a binding pocket (Pocket #2) defined by structure coordinates of Cdk2 amino acid residues 13-18, 20, 28, 31, 33, 51, 80-89, 131-136, and 145; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes: (i) a machine-readable data storage medium comprising a data storage material encoded with machine-readable data, wherein said data comprises the structure coordinates of Cdk2 amino acid residues 13-18, 20, 28, 31, 33, 51, 80-89, 131-136, and 145; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

The invention also provides methods for designing, evaluating and identifying compounds which bind to the aforementioned binding pockets. Such compounds are potential inhibitors of Cdk activity. Other embodiments of the invention are disclosed infra.

BRIEF DESCRIPTION OF THE DRAWINGS

The present invention is further described below with reference to the following non-limiting examples and with reference to the following figures, in which:

FIG. 1. Crystal structures of Cyclin A/Cdk2 and Cyclin A/Cdk2/p27 complexes reveal a target ("Pocket #1") for small molecule binding. Cyclin A/Cdk2 complexes are shown as ribbon diagrams (top left) and as space-filled models (bottom left). The Cyclin A and Cdk2 subunits and the Tyr$^{15}$ (Y15) and Arg$^{36}$ (R36) residues of Cdk2 are denoted by arrows. Note that Y15 and R36 are tightly packed together and the Y15 sidechain is inserted into the core of the protein. In contrast, note that in the Cyclin A/Cdk2/p27 structure (right panels) the Y15 and R36 residues of Cdk2 are separated by a cleft. This cleft is specific to the Cyclin A/Cdk2/p27 complex and was targeted in in silico molecular docking studies as described herein.

DETAILED DESCRIPTION OF THE INVENTION

Figure 2:
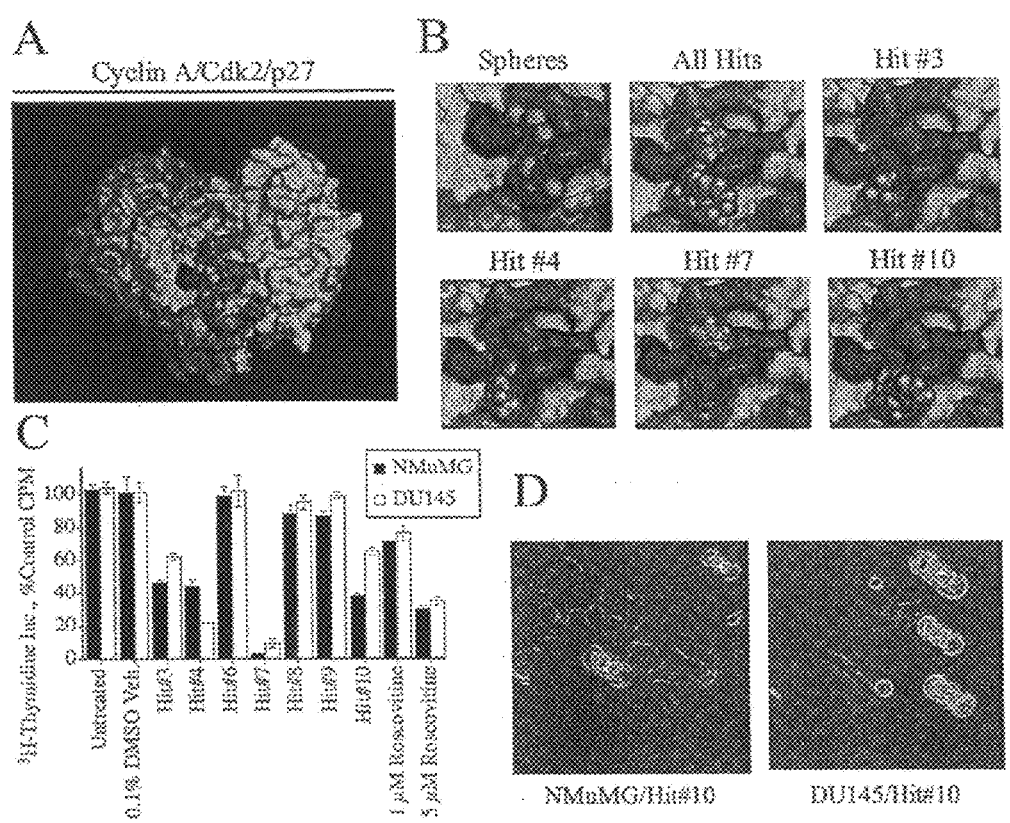
FIG. 2. In silico molecular docking and preliminary analysis of potential Cyclin/Cdk2 inhibitors. (A) Cyclin A/Cdk2/p27 complex with spheres docked into the binding pocket (Pocket #1) and the pocket enclosed in a scoring grid (rectangular box). (B) Binding cleft shown filled with spheres, the top 10 hits superimposed into the binding pocket (All Hits), and the predicted mode of binding of individual hits in the Cyclin A/Cdk2/p27 pocket (Hits #3-10). (C) NMuMG (black bars) or DU145 cells (open bars) were treated for 24 hours with 100 μM of the indicated compounds and $^{3}$H-thymidine incorporation was measured to assess rates of cell proliferation. Roscovitine is a known Cdk inhibitor and was included as a positive control. DMSO (0.1%) was included as a vehicle control. (D) Morphological change induced by 100 μM Hit #10 in NMuMG and DU145 cells after treatment for 24 hours.

The present inventors have now discovered a therapeutic strategy that combines the antiproliferative actions of TGFβ and rapamycin using a (preferably small molecule) compound, preferably a compound that can be used systemically. Such a small molecule can potentially act directly on the relevant cell cycle machinery rather than at the upstream end of a multi-step branched signaling pathway, preferably providing greater specificity and exhibiting fewer of the negative side effects associated with TGFβ and rapamycin.

The present invention relates, at least in part, to the discovery that the complex of Cyclin A/Cdk2/p27 includes at least two binding pockets to which small molecules can be targeted to inhibit Cdk activity. In certain embodiments, the compound is capable of stabilizing an inactive conformation of a cyclin-dependent kinase or a complex of a cyclin-dependent kinase and a cyclin, resulting in inhibition of cdk activity.

1. Definitions

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors or cancers (e.g., brain, lung (small cell and non-small cell), ovary, prostate, breast or colon) or other carcinomas or sarcomas (e.g., leukemia, lymphoma).

The term "cyclic-dependent kinase" refers to any of a family of proteins capable of complexing with a cyclin and capable of catalyzing phosphorylation of a substrate. Cyclin-dependent kinases (also called cdks) are known in the art and include cdk1, cdk2, cdk4, and cdk6. A preferred cdk is cdk 2.

The term "cyclic-dependent kinase downregulator compound" refers to a compound capable of decreasing the amount of or downregulating the expression of at least one cyclin-dependent kinase in a cell or tissue, preferably by at least about 10%, 20%, 30%, 40% 50%, 60%, 70%, 80%, 90%, or 95%, compared to an inactive control.

The language "a p27-induced binding pocket of a cyclin dependent kinase" refers to a binding pocket of a cyclin dependent kinase that is exposed or accessible to a ligand only when p27 (or another cdk inhibitor such as p21 or p57) is bound to the cdk; the cdk may in addition be bound to a cyclin to form a cyclin/cdk/inhibitor complex in which the p27- induced binding pocket is or becomes accessible. Pocket #1, as described herein, is a p27=induced binding pocket of a cyclin dependent kinase.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of stabilizing the interaction of a cyclin/cyclin-dependent kinase complex and p27" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention of the invention, such as human and non-human animals. Preferred humans include human patients suffering from or prone to suffering from a cell proliferative disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides compounds capable of inhibiting (directly or indirectly) Cdk activity.

In one embodiment, the invention provides a compound capable of binding to a p27-induced binding pocket of a cyclin dependent kinase such as cdk2, e.g., a pocket formed as a result of the binding of an inhibitor such as p27 to a cyclin dependent kinase or a complex of a cyclin dependent kinase with a cyclin, e.g., Pocket #1. In one embodiment, the invention provides a compound of the formula A-D, in which A is an aromatic moiety capable of interacting with a p27-induced binding pocket of a cyclin dependent kinase and D is a hydrogen bond donor or acceptor; and pharmaceutically acceptable esters, salts, and prodrugs thereof.

Certain preferred compounds include compounds 3, 4 and 7; these compounds are shown below:

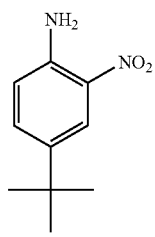

Compound 3 (4-t-butyl-2-nitro-aniline)

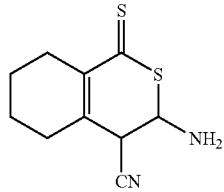

Compound 4
(3-amino-1-sulfanylidene-5,6,7,8-tetrahydroisothiochromene-4-carbonitrile)

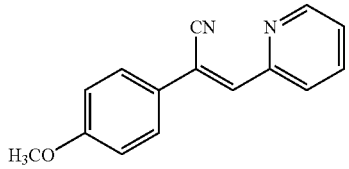

Compound 7 (2-(4-methoxyphenyl)-3-pyridin-2-yl-prop-2-enenitrile)

In another embodiment, the invention provides a compound capable of binding to a pocket adjacent to or overlapping with a binding site of an inhibitor such as p27 to a cyclin dependent kinase or a complex of a cyclin dependent kinase with a cyclin (e.g., Pocket #2), and thereby mimicking p27 activity to inhibit cyclin-dependent kinase activity.

In certain embodiments of this embodiment of the invention, the compound is compound 7 (above), Compound 1 or Compound 11:

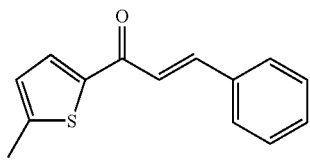

Compound 1 (1-(5-Methyl-thiophen-2-yl)-3-phenyl-propenone)

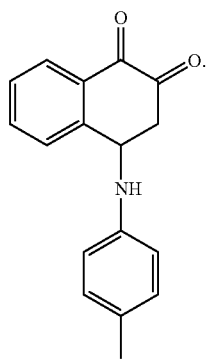

Compound 11 (4-p-Tolylamino-[1,2]naphthoquinone)

Addition embodiments include the following compounds:

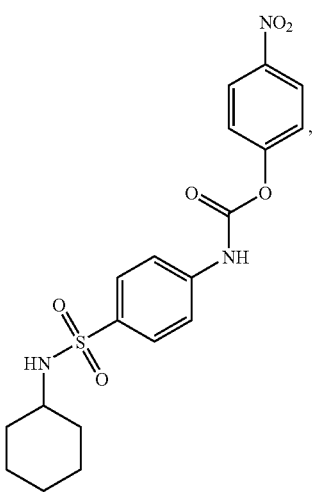

(Compound 21,
4-[3-(4-Amino-phenyl)-ureido]-N-cyclohexyl-benzenesulfonamide)

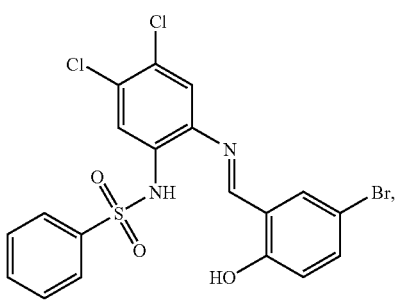

(Compound 22,
N-{4,5-Dichloro-2-[(5-bromo-2-hydroxy-benzylidene)-amino]-phenyl}-benzenesulfonamide)

-continued

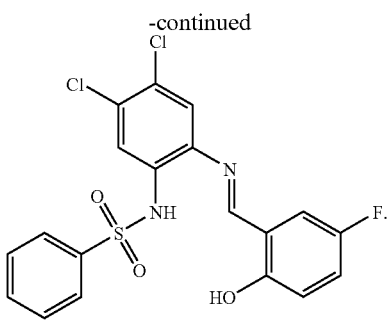

(Compound 23,
N-{4,5-Dichloro-2-[(5-fluoro-2-hydroxy-benzylidene)-amino]-phenyl}-benzenesulfonamide)

The invention also relates to the pharmaceutically acceptable salts and esters of the above-mentioned compounds.

In certain embodiments, the compound is not 1-(N',N'-Dimethyl-hydrazino)-7-methoxy-xanthen-9-one (Compound 2).

Additional compounds of the invention are shown in Tables 1 and 2, infra.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds which associate with or bind to a Cdk-related binding pocket (e.g., Pocket #1 or Pocket #2) produced or identified by the methods described herein.

In another aspect, the invention provides polypeptides useful for screening for compounds useful for treatment of proliferative disorders. A polypeptide of the invention includes a p27-binding pocket of a cyclin dependent kinase (e.g., residues Valine 16-Phenylalanine 146 of cdk2). A polypeptide of the invention can be a fusion protein, e.g., a p27-binding pocket moiety fused with a detectable reporter moiety such as green fluorescent protein ( ), or labeled with a detectable tag such as a fluorescent label, a radiolabel, and the like. Such a fusion protein can be used in screening for compounds capable of stabilizing an interaction between a cyclin dependent kinase and p27.

Additional preferred compounds include cdk downregulator compounds which decrease the level, activity, or expression of one or more cdks (including, e.g., Cdk1, Cdk2, Cdk4, or Cdk6) in a cell or tissue. Such compounds can be identified, e.g., using the methods described herein.

3. Uses of the Compounds of the Invention

As described herein below, it has now been found that certain compounds of the invention and analogs can stabilize the interaction of a cyclin dependent kinase (or a cyclin/cyclin-dependent kinase complex) and a cdk inhibitor such as p27 (or related inhibitors such as p21 or p57), e.g., by binding to a binding pocket of a complex of a cyclin dependent kinase with the inhibitor (e.g., Pocket #1), and/or downregulate expression of a cyclin-dependent kinase, and thereby treat disorders of cell proliferation, including cancer. As described in more detail, infra, and without being bound by any particular theory, in certain embodiments of the invention, it is believed that compounds capable of binding to a binding pocket present in a complex of a cyclin-dependent kinase with p27 (but not present or not accessible in the unbound cyclin dependent-kinase, e.g., Pocket #1)) can stabilize the cdk-p27 interaction, thereby inhibiting the activity of the cdk.

Thus, in one embodiment, the invention provides methods for treating a subject for a cell proliferative disorder, by administering to the subject an effective amount of a compound capable of stabilizing a complex of a cyclin dependent kinase and a cdk inhibitor such as p27 (or related inhibitors such as p21 or p57). A cell proliferative disorder includes cancer. In certain embodiments, the subject is a mammal, e.g., a primate, e.g., a human.

In this embodiment, the compounds of the invention may either directly or indirectly stabilize the interaction of a cyclin/cyclin-dependent kinase complex and a cdk inhibitor such as p27. A cell undergoing uncontrolled proliferation can be contacted with a compound of the invention to inhibit cell proliferation. Contacting cells or administering the compounds of the invention to a subject is one method of treating a cell or a subject suffering from or susceptible to unwanted or undesired cell proliferation or a cell proliferative disorder.

In one embodiment, a method of treating a subject suffering from or susceptible to unwanted or undesired cell proliferation or a cell proliferative disorder includes administering to a subject in need thereof a therapeutically effective amount of a compound capable of stabilizing the interaction of a cyclin dependent kinase with a cdk inhibitor such as p27, to thereby treat the subject suffering from or susceptible to unwanted or undesired cell proliferation or a cell proliferative disorder. Exemplary compounds capable of stabilizing the interaction of a cyclin dependent kinase with a cdk inhibitor include compounds described herein.

It has also now been found that certain compounds of the invention can bind to a binding pocket of a cyclin/cyclin-dependent kinase complex (Pocket #2), and thereby treat disorders of cell proliferation, including cancer.

Thus, in one embodiment, the invention provides methods for treating a subject for a cell proliferative disorder, by administering to the subject an effective amount of a compound capable of binding to a binding pocket of a cyclin/cyclin-dependent kinase complex (Pocket #2).

In this embodiment, the compounds of the invention may either directly or indirectly inhibit the activity of a cyclin/cyclin-dependent kinase complex. A cell undergoing uncontrolled proliferation can be contacted with a compound of the invention to inhibit cell proliferation. Contacting cells or administering the compounds of the invention to a subject is one method of treating a cell or a subject suffering from or susceptible to unwanted or undesired cell proliferation or a cell proliferative disorder.

In one embodiment, a method of treating a subject suffering from or susceptible to unwanted or undesired cell proliferation or a cell proliferative disorder includes administering to a subject in need thereof a therapeutically effective amount of a compound capable of compound capable of binding to a binding pocket of a cyclin/cyclin-dependent kinase complex (Pocket #2), under conditions such that the subject is treated. Exemplary compounds capable of compound capable of binding to a binding pocket of a cyclin/cyclin-dependent kinase complex (Pocket #2) include compounds described herein.

A further aspect presents a method of treating a subject suffering from or susceptible to cancer, including administering to the subject an effective amount of a compound of the invention (e.g., a compound capable of stabilizing a complex of a cyclin dependent kinase and a cdk inhibitor such as p27, a compound capable of binding to a binding pocket of a cyclin/cyclin-dependent kinase complex (Pocket #2), a compound capable of downregulating cdk expression, or a compound of any formula herein or otherwise described herein) to thereby treat the subject suffering from or susceptible to cancer.

In certain embodiments, the methods of the invention include administering to a subject a therapeutically effective amount of a compound of the invention in combination with another pharmaceutically active compound. Examples of pharmaceutically active compounds include compounds known to treat cell proliferative disorders, e.g., imatinib (Gleevec). Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional cancer chemotherapeutics. Conventional treatment regimens for leukemia and for other tumors include radiation, drugs, or a combination of both. In addition to radiation, the following drugs, usually in combinations with each other, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative-disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., a compound capable of stabilizing a complex of a cyclin dependent kinase and p27, a compound capable of downregulating cdk expression, or a compound of any formula herein or otherwise described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

Yet another aspect presents a method to identify a compound that modulates the interaction of a cyclin dependent kinase with a cdk inhibitor such as p27. The method may include obtaining the crystal structure of a cyclin dependent kinase (optionally complexed with a cyclin) or obtaining the information relating to the crystal structure of a cyclin dependent kinase (optionally complexed with a cyclin), in the presence and/or absence of the cdk inhibitor. Compounds may then be computer modeled into or on the p27 binding site of the crystal structure to predict stabilization of the interaction between the cyclin dependent kinase and the cdk inhibitor. Once potential inhibitory compounds are identified, the compounds may be screened using cellular assays, such as the ones identified below in the Examples and competition assays known in the art. Compounds identified that modulate the interaction of a cyclin dependent kinase with a cdk inhibitor such as p27 could be agonists or antagonists (more preferably agonists) of cdk inhibitor (e.g., p27) binding and could be useful therapeutic agents.

In another aspect, a compound of the invention is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In yet another aspect, a method of treating a subject suffering from or susceptible to a cell proliferative disorder comprising administering to a subject in need thereof a therapeutically effective amount of a compound capable of downregulating the expression of a cyclin dependent kinase (or kinases), to thereby treat the subject suffering from or susceptible to a cell proliferative disorder. Upon identification of a subject suffering from or susceptible to a cell proliferative disorder, a compound capable of downregulating the expression of a cyclin dependent kinase is administered to the subject.

In another aspect, the invention provides methods for inhibiting cell proliferation. In one embodiment, a method of inhibiting cell proliferation (or a cell proliferative disorder) according to the invention includes contacting cells with a compound capable of stabilizing an interaction between a cyclin dependent kinase and a cdk inhibitor such as p27. In another embodiment, a method of inhibiting cell proliferation (or a cell proliferative disorder) according to the invention includes contacting cells with a compound capable of downregulating the expression of a cyclin dependent kinase(s) in the cells. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a cell proliferative disorder in a subject include administering an effective amount of a compound of the invention (i.e., a compound capable of stabilizing an interaction of a cyclin dependent kinase with a cdk inhibitor such as p27) to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to a conditions capable of increasing susceptibility to a cell proliferative disorder, e.g., exposure to carcinogens or to ionizing radiation.

In one aspect, a method of monitoring the progress of a subject being treated with a downregulator of expression of a cyclin dependent kinase includes determining the pretreatment status (e.g., size, growth rate, or invasiveness of a tumor) of the cell proliferative disorder, administering a therapeutically effective amount of a downregulator of expression of a cyclin dependent kinase to the subject, and determining the status of the cell proliferative disorder after an initial period of treatment with the downregulator of expression of a cyclin dependent kinase, wherein the modulation of the status indicates efficacy of the treatment.

In one aspect, a method of monitoring the progress of a subject being treated with a compound capable of stabilizing an interaction of a cyclin dependent kinase and a cdk inhibitor such as p27 includes determining the pre-treatment status (e.g., size, growth rate, or invasiveness of a tumor) of the cell proliferative disorder, administering a therapeutically effective amount of a compound capable of stabilizing an interaction of a cyclin dependent kinase and a cdk inhibitor to the subject, and determining the status (e.g., size, growth rate, or invasiveness of a tumor) of the cell proliferative disorder after an initial period of treatment with the compound capable of stabilizing an interaction of a cyclin dependent kinase and a cdk inhibitor, wherein the modulation of the status indicates efficacy of the treatment.

In one aspect, methods of selecting a subject suffering from or susceptible to a cell proliferative disorder for treatment with a compound capable of stabilizing an interaction of a cyclin dependent kinase and a cdk inhibitor such as p27 comprise determining the pre-treatment status (e.g., size, growth rate, or invasiveness of a tumor) of the cell proliferative disorder, administering a therapeutically effective amount of a compound capable of stabilizing an interaction of a cyclin dependent kinase and a cdk inhibitor to the subject, and determining the status (e.g., size, growth rate, or invasiveness of a tumor) of the cell proliferative disorder after an initial period of treatment with the compound capable of stabilizing an interaction of a cyclin dependent kinase and p27, wherein the modulation of status is an indication that the cell proliferative disorder is likely to have a favorable clinical response to treatment with a compound capable of stabilizing an interaction of a cyclin dependent kinase and a cdk inhibitor.

The subject may be at risk of a cell proliferative disorder, may be exhibiting symptoms of a cell proliferative disorder, may be susceptible to a cell proliferative disorder and/or may have been diagnosed with a cell proliferative disorder.

The initial period of treatment may be the time in which it takes to establish a stable and/or therapeutically effective blood serum level of the compound capable of stabilizing an interaction of a cyclin dependent kinase and a cdk inhibitor, or the time in which it take for the subject to clear a substantial portion of the compound, or any period of time selected by the subject or healthcare professional that is relevant to the treatment.

If the modulation of the status indicates that the subject may have a favorable clinical response to the treatment, the subject may be treated with the compound. For example, the subject can be administered therapeutically effective dose or doses of the compound.

In another aspect, methods for evaluating a test compound comprise contacting a cyclin dependent kinase (e.g., cdk2) with a test compound in the presence of a cdk inhibitor such as p27 (optionally in the presence of a cyclin), and evaluating the stability of a cyclin dependent kinase-cdk inhibitor complex (or cyclin-cyclin dependent kinase-cdk inhibitor complex) following contact, wherein a change in the stability of the complex relative to a reference value is an indication that the test compound modulates the stability of the complex.

The cyclin dependent kinase-cdk inhibitor complex (or cyclin-cyclin dependent kinase-cdk inhibitor complex) may be modeled in silico, or may be a complex within a cell, isolated from a cell, recombinantly expressed, purified or isolated from a cell or recombinant expression system or partially purified or isolated from a cell or recombinant expression system.

In another aspect, methods for evaluating a test compound comprise contacting a cyclin dependent kinase (e.g., cdk2) with a test compound in the presence of a cdk inhibitor such as p27 (optionally in the presence of a cyclin), and evaluating the stability of a cyclin dependent kinase-cdk inhibitor complex (or cyclin-cyclin dependent kinase-cdk inhibitor complex) following contact, wherein a change in the stability of the complex relative to a reference value is an indication that the test compound modulates the stability of the complex.

The cyclin dependent kinase-cdk inhibitor complex (or cyclin-cyclin dependent kinase-cdk inhibitor complex) may be modeled in silico, or may be a complex within a cell, isolated from a cell, recombinantly expressed, purified or isolated from a cell or recombinant expression system or partially purified or isolated from a cell or recombinant expression system.

In another aspect, the invention provides methods for downregulating expression of a cyclin dependent kinase in a cell. The methods include contacting the cell with an effective amount of a compound capable of downregulating expression of a cyclin dependent kinase, such that expression of a cyclin dependent kinase is downregulated. The contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, the invention provides methods for stabilizing an interaction of a cyclin dependent kinase (or a cyclin-cyclin dependent kinase complex) with a cdk inhibitor such as p27. The methods include contacting the cyclin dependent kinase (or cyclin-cyclin dependent kinase complex), in the presence of the cdk inhibitor, with a compound capable stabilizing an interaction of a cyclin dependent kinase (or a cyclin-cyclin dependent kinase complex) with the cdk inhibitor, such that an interaction of a cyclin dependent kinase (or a cyclin-cyclin dependent kinase complex) with the cdk inhibitor is stabilized.

The cyclin dependent kinase (or cyclin-cyclin dependent kinase complex) may be within a cell, isolated from a cell, recombinantly expressed, purified or isolated from a cell or recombinant expression system or partially purified or isolated from a cell or recombinant expression system.

The contacting may be in vitro, e.g., by addition of the compound to a solution containing a purified cyclin dependent kinase (or cyclin-cyclin dependent kinase complex), or, if the cyclin dependent kinase (or cyclin-cyclin dependent kinase complex) is present in cells, by adding the compound to a fluid surrounding the cells, for example, to the growth media in which the cells are living or existing. The contacting may also be by directly contacting the compound to the cells. Alternatively, the contacting may be in vivo, e.g., by passage of the compound through a subject; for example, after administration, depending on the route of administration, the compound may travel through the digestive tract or the blood stream or may be applied or administered directly to cells in need of treatment.

Kits of the invention include kits for treating a cell proliferative disorder in a subject. The invention also includes kits for downregulating expression of a cyclin dependent kinase, stabilizing an interaction of a cyclin dependent kinase (or a cyclin-cyclin dependent kinase complex), assessing the efficacy of a treatment for a cell proliferative disorder in a subject, monitoring the progress of a subject being treated for a cell proliferative disorder, selecting a subject with a cell proliferative disorder for treatment according to the invention, and/or treating a subject suffering from or susceptible to a cell proliferative disorder. The kit may include a compound of the invention, for example, a compound of formula I, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

The present method can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179,109—fetal rat tissue culture), or other mammalian (See e.g. U.S. Pat. No. 5,089,517—fetal mouse tissue culture) or non-mammalian animal models.

Alternatively, the effects of compound of the invention can be characterized in vivo using animals models.

4. Pharmaceutical Compositions

The invention also provides a pharmaceutical composition, comprising an effective amount of a compound of the invention (e.g., a compound capable of stabilizing a complex of a cyclin dependent kinase and a cdk inhibitor such as p27, a compound capable of down-regulating cdk expression, or a compound of any formula herein or otherwise described herein) and a pharmaceutically acceptable carrier. In a further embodiment, the effective amount is effective to treat a cell proliferative disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium Stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, Water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001—about 10 mg/kg or about 0.001 mg—about 100 mg/kg of body weight. Ranges intermediate to the above-recited values are also intended to be part of the invention.

6. Screening Methods and Systems

In another aspect, the invention provides a machine readable storage medium which comprises the structural coordinates of either one or both of the binding pockets identified herein, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Such compounds are potential inhibitors of Cdk activity.

According to another aspect, the invention provides a computer for producing a three-dimensional representation of a molecule or molecular complex, wherein said molecule or molecular complex comprises a binding pocket (Pocket #1) defined by structure coordinates of Cdk2 amino acid residues 14-19, and 30-37, and p27 amino acids 67, 78 81, and 86-92; or b) a three-dimensional representation of a homologue of said molecule or molecular complex, wherein said homologue comprises a binding pocket that has a root mean square deviation from the backbone atoms of said amino acids of not more than about 2.0 (more preferably not more than 1.5) angstroms, wherein said computer comprises:

(i) a machine-readable data storage medium comprising a data storage material encoded with machine-readable data, wherein said data comprises the structure coordinates of Cdk2 amino acid residues 14-19 and 30-37, and p27 amino acids 67, 78-81, and 86-92;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

According to another aspect, the invention a computer for producing a three-dimensional representation of a molecule or molecular complex, wherein said molecule or molecular complex comprises a binding pocket (Pocket #2) defined by structure coordinates of Cdk2 amino acid residues 13-18, 20, 28, 31, 33, 51, 80-89, 131-136, 145; or b) a three-dimensional representation of a homologue of said molecule or molecular complex, wherein said homologue comprises a binding pocket that has a root mean square deviation from the backbone atoms of said amino acids of not more than about 2.0 (more preferably not more than 1.5) angstroms, wherein said computer comprises:

(i) a machine-readable data storage medium comprising a data storage material encoded with machine-readable data, wherein said data comprises the structure coordinates of Cdk2 amino acid residues 13-18, 20, 28, 31, 33, 51, 80-89, 131-136, 145;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

Thus, the computer produces a three-dimensional graphical structure of a molecule or a molecular complex which comprises a binding pocket.

In another embodiment, the invention provides a computer for producing a three-dimensional representation of a molecule or molecular complex defined by structure coordinates of all of the Cdk2 amino acids, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms In exemplary embodiments, the computer or computer system can include components which are conventional in the art, e.g., as disclosed in U.S. Pat. Nos. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding pocket of a cyclin/Cdk or cyclin/Cdk/p27 complex may inhibit Cdk activity, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket defined by structure coordinates of Cdk2 amino acid residues 14-19, and 30-37, and p27 amino acids 67, 78 81, and 86-92, as described herein, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding pocket of the molecule or molecular complex; and ii) analyzing the results of the fitting operation to quantify the association between the chemical entity and the binding pocket. This embodiment relates to evaluating the potential of a chemical entity to associate with or bind to a binding pocket referred to herein as "Pocket #1". The term "chemical entity", as used herein, refers to chemical compounds, complexes of at least two chemical compounds, and fragments of such compounds or complexes.

In an alternate embodiment, the same steps indicated above are used in a method for evaluating the potential of a chemical entity to associate with or bind to a) a molecule or molecular complex comprising a binding pocket defined by structure coordinates of Cdk2 amino acid residues 13-18, 20, 28, 31, 33, 51, 80-89, 131-136, 145, as described herein, or b) a homologue of said molecule or molecular complex, wherein said homologue comprises a binding pocket that has a root mean square deviation from the backbone atoms of said amino acids of not more than 2.0 (more preferably not more than 1.5) angstroms. This embodiment relates to evaluating the potential of a chemical entity to associate with or bind to a binding pocket referred to herein as "Pocket #2".

In certain embodiments, the method evaluates the potential of a chemical entity to associate with a molecule or molecular complex defined by structure coordinates of all of the amino acids of Cdk2 and/or p27, and optionally further including cyclin A, as described herein, or a homologue of said molecule or molecular complex having a root mean square deviation from the backbone atoms of said amino acids of not more than 2.0 (more preferably not more than 1.5) angstroms.

In a further embodiment, the structural coordinates one of the binding pockets described herein can be utilized in a method for identifying a potential agonist or antagonist of a molecule comprising a Cdk binding pocket. This method comprises the steps of:

a) using the atomic coordinates of Cdk2 amino acid residues 14-19 and 30-37, and p27 amino acids 67, 78-81, and 86-92, as described herein, with a root mean square deviation from the backbone atoms of said amino acids of not more than about 2.0 (more preferably not more than 1.5) angstroms, to generate a three-dimensional structure of molecule comprising a Cdk2 binding pocket;

b) employing the three-dimensional structure to design or select the potential agonist or antagonist. The method further includes the optional steps of c) synthesizing the agonist or antagonist; and d) contacting the agonist or antagonist with the molecule to determine the ability of the potential agonist or antagonist to interact with the molecule.

These methods are designed to identify agonists and antagonists that associate with a Cdk2 binding pocket (Pocket #1).

Alternatively, the atomic coordinates of the Cdk2 amino acid residues 13-18, 20, 28, 31, 33, 51, 80-89, 131-136, 145, may be used in step a), above, to generate a three-dimensional structure of molecule comprising a second Cdk2 binding pocket (Pocket #2).

The present inventors' elucidation of heretofore unknown binding pockets in the cyclin A/Cdk2 (and optionally p27) complex provides the necessary information for designing new chemical entities and compounds that may interact with cyclin dependent kinases such as Cdk2, in whole or in part, and may therefore modulate (e.g., inhibit) the activity of cyclin dependent kinases.

The design of compounds that bind to or inhibit Cdk2-related binding pockets according to this invention generally involves consideration of several factors. First, the entity must be capable of physically and structurally associating with parts or all of the Cdk2-related binding pockets. Non-covalent molecular interactions important in this association include hydrogen bonding, van der Waals interactions, hydrophobic interactions and electrostatic interactions. Second, the entity must be able to assume a conformation that allows it to associate with the Cdk2-related binding pocket(s) directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on a Cdk-related binding pocket may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule to inhibit Cdk activity, e.g., using assays described herein or known in the art. In this manner, synthesis of inoperative compounds may be avoided.

A potential inhibitor of a Cdk-related binding pocket may be computationally evaluated by means of a series of steps in which chemical entities or fragments are screened and selected for their ability to associate with the Cdk-related binding pockets.

One skilled in the art may use one of several methods to screen chemical entities or fragments for their ability to associate with a Cdk-related binding pocket. This process may begin by visual inspection of, for example, a Cdk-related binding pocket on the computer screen based on the Cdk and/or p27 structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention [see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein (see, e.g., Examples 1 and 2). Many thousands of compounds can be rapidly screened and the best virtual compounds can be selected for further screening (e.g., by synthesis and in vitro testing). Small molecule databases can be screened for chemical entities or compounds that can bind, in whole or in part, to a Cdk binding pocket. In this screening, the quality of fit of such entities to the binding site may be judged either by shape complementarity or by estimated interaction energy.

EXAMPLES

The invention is further illustrated by the following examples which are intended to illustrate but not limit the scope of the invention.

Example 1

To identify novel small molecule inhibitors of Cyclin/Cdk complexes we investigated structural differences between Cyclin A/Cdk2 complexes and Cyclin A/Cdk2/p27 complexes, using the solved crystal structures of these complexes [17, 18]. This analysis demonstrated that p27 binding induces a conformational change that opens a pocket that is flanked by residues from p27 on the top and bottom (e.g., residues 67, 78-81, and 86-92 of p27) and residues including residues 14-19 and 30-37 (including Arg[36] and Tyr[15]) from Cdk2 on either side of the pocket (FIG. 1). The computer program suite DOCK was used to characterize all of the potential binding pockets on the Cyclin A/Cdk2/p27 complex molecular surface. The program identified the Cyclin A/Cdk2/p27 binding pocket as favorable for molecular docking studies using small molecule compound libraries. A molecule that binds the pocket present in the Cyclin A/Cdk2/p27 complex, but not in the Cyclin A/Cdk2 complex, (this binding pocket is also referred to as "Pocket #1 herein) is predicted to "lock" Cdk2 into an inactive conformation.

A rapid structure based approach was utilized to "screen" compounds. In silico molecular docking was performed with the DOCK program package [19, 20] using the Cdk2/p27 pocket described above and an National Cancer Institute/Developmental Therapeutics Program (NCI/DTP) small molecule library of 140,000 compounds (FIGS. 2A, B). The 11 molecules with the top estimated binding energies are shown in Table 1.

TABLE 1

| Rank | Mol Weight | Energy Score | Structure |
|---|---|---|---|
| 1 | 228 | −16.679359 | 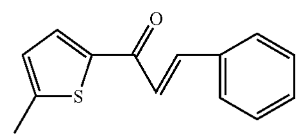 [SMILES: Cc1ccc(C(=O)/C=C/c2ccccc2)s1] |
| 2 | 312 | −16.488708 | 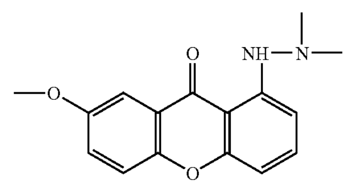 |
| 3 | 194 | −16.355101 | 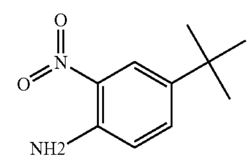 |
| 4 | 222 | −15.208357 | 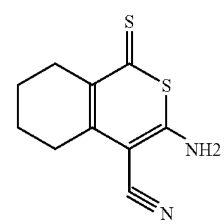 [SMILES: N#Cc1c(N)sc(=S)c2c1CCCC2] |
| 5 | 176 | −15.068427 | 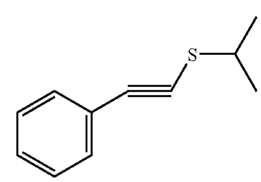 |
| 6 | 148 | −14.804389 | 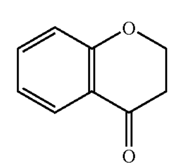 [SMILES: O=C1CCOc2ccccc21] |
| 7 | 236 | −14.166451 | 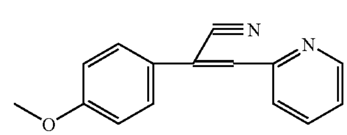 [SMILES: COc1ccc(C(C#N)=Cc2ccccn2)cc1] |

TABLE 1-continued

| Rank | Mol Weight | Energy Score | Structure |
|---|---|---|---|
| 8 | 171 | −13.930276 | (Not Available) |
| 9 | 207 | −13.864219 | [structure: dichlorohydroxybenzoic acid] |
| 10 | 274 | −13.493698 | [structure: diphenyl sulfite Ph-O-S(=O)-O-Ph] |
| 11 | 263 | −13.370044 | [structure: 4-(p-tolylamino)naphthalene-1,2-dione] |

Example 2

The NCI/DTP maintains a repository of approximately 139,644 samples (i.e., the plated compound set) which are non-proprietary and offered to the research community for discovery and development of new agents for the treatment of cancer, AIDS, or opportunistic infections afflicting subjects with cancer or AIDS. The three-dimensional coordinates for the NCI/DTP plated compound set was obtained in the MDL SD format (http://www.chm.tu-dresden.de/edv/vamp65/REFERS/vr_03d.htm) and converted to the mol2 format by the DOCK utility program SDF2MOL2. Partial atomic charges, salvation energies and van der Waals parameters for the ligands were calculated using SYBDB and added to the plated compound set mol2 files.

Example 3

All docking calculations were performed with the Oct. 15, 2002, development version of DOCK v5.1.0 or later versions. The general features of DOCK include rigid orientating of ligands to receptor spheres, AMBER (http://neumann.cem.msu.edu/QBMI/DOCK_v5.1.0.htm) energy scoring, GB/SA solvation scoring, contact scoring, internal non-bonded energy scoring, ligand flexibility and both rigid and torsional simplex minimization. The coordinates for the crystal structure of human Cdk2 complexed to Cyclin A and p27, PDB code 1JSU [18] (accessed at http://www.rcsb.org/pdb/explore/explore.do?structureId=1JSU, incorporated herein by reference), as shown in the PDB Appendix attached hereto (incorporated herein by reference) is utilized in the molecular docking calculations. To prepare the site for docking, all water molecules are removed. Protonation of receptor residues is performed with Sybyl6.7 (Tripos, St. Louis, Mo.). The structure is explored using sets of spheres to describe potential binding pockets. The number of orientations per molecule is set at 100. Intermolecular AMBER energy scoring (vdW+ Coulombic), contact scoring and bump filtering are implemented in DOCK5.2.1 [28].

Example 4

Figure 3:
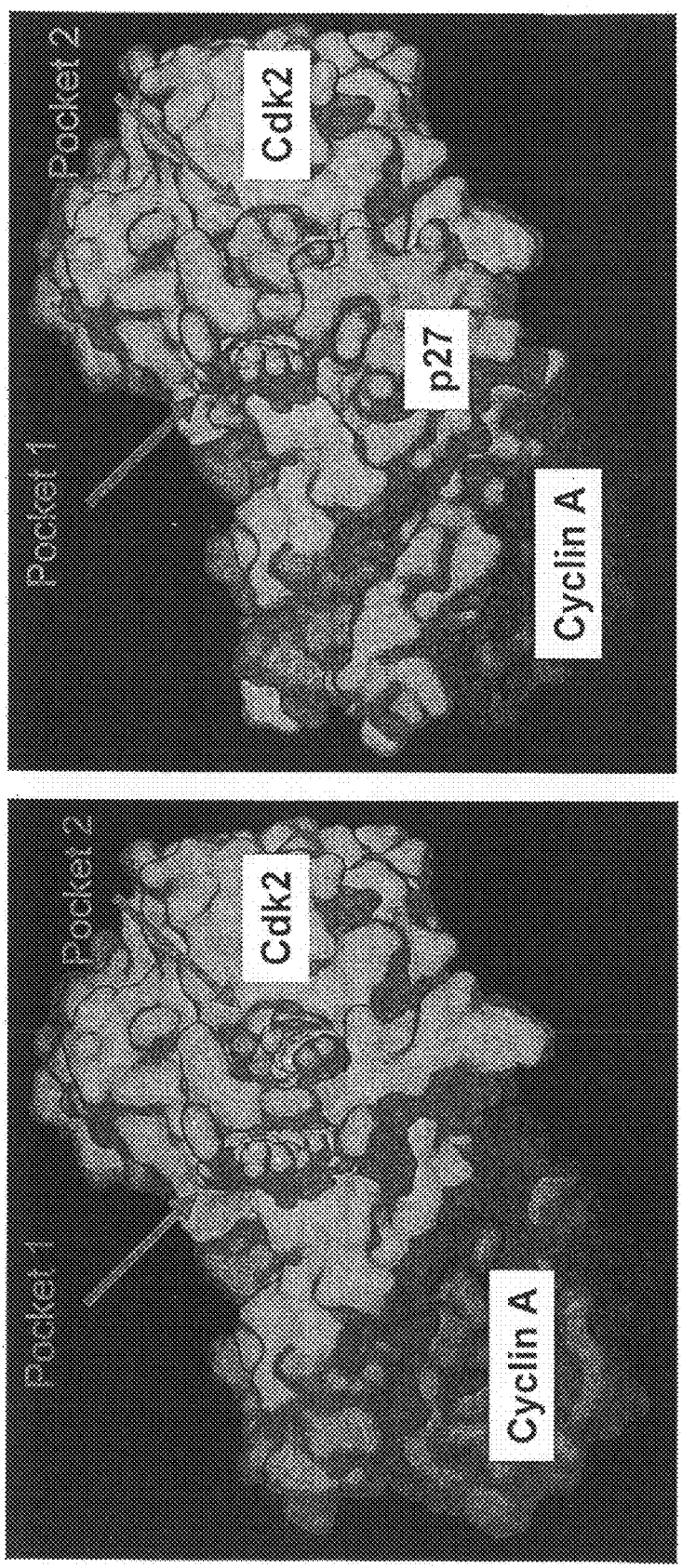
FIG. 3. Crystal structure of the Cyclin A/Cdk2/p27 complex with p27 deleted in silico reveal a second target ("Pocket #2") for small molecule binding. The p27 subunit of the Cyclin A/Cdk2/p27 complex was deleted using the PyMol program and the SPHGEN program was used to identify drug binding pockets within the p27 binding site. Such compounds are predicted to mimic p27 in their ability to induce a conformational change in Cdk2 and to inhibit Cdk2 activity. The identified pocket, Pocket #2, was targeted in molecular docking studies.

Novel Cdk inhibitors were identified using molecular docking, starting with a Cyclin A/Cdk2/P27 complex as described in Examples 1-3, supra. P27 was deleted in silico from the crystal structure of the Cyclin A/Cdk2/p27 complex. A pocket was identified that overlapped with the p27 binding site on Cdk2 and had the characteristics of a good drug binding pocket as determined using the SPHGEN computer program (FIG. 3). In silico molecular docking was performed to identify molecules that would bind to this pocket ("Pocket. #2") with high affinity. These compounds were demonstrated to inhibit the proliferation of BT549 human breast cancer cells in $^3$H-thymidine incorporation DNA synthesis assays (see Example 6, infra). Many of these "Pocket #2" compounds exhibit similar activity to the "Pocket #1" compounds, such as Compound #7, in the extent to which they block cell proliferation. The compounds predicted to bind to Pocket #2 also showed potency that was similar to Compound 7. The top-ranked Pocket #2 compounds based on computer-estimated interactions involving total energy score (ES or Energy Score Hits) are shown below.

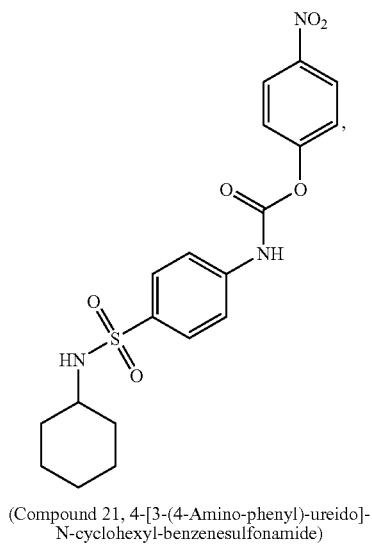

(Compound 21, 4-[3-(4-Amino-phenyl)-ureido]-N-cyclohexyl-benzenesulfonamide)

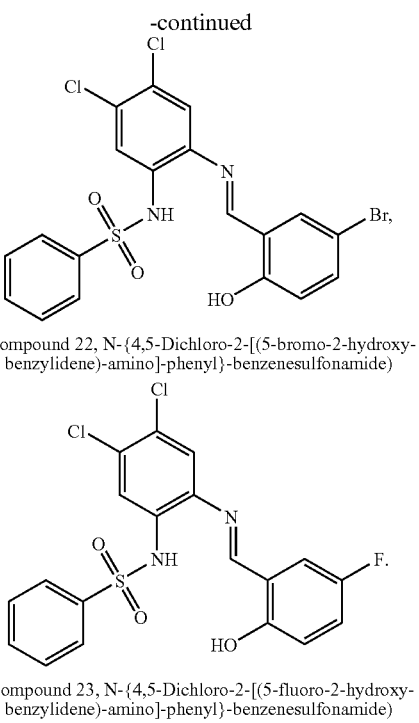

(Compound 22, N-{4,5-Dichloro-2-[(5-bromo-2-hydroxy-benzylidene)-amino]-phenyl}-benzenesulfonamide)

(Compound 23, N-{4,5-Dichloro-2-[(5-fluoro-2-hydroxy-benzylidene)-amino]-phenyl}-benzenesulfonamide)

The top-ranked Pocket #2 compounds based on computer-estimated interactions involving van der Waal's forces (VDW or VDW Hits) include the three compounds shown above and others as shown in Table 2 (below).

TABLE 2

| VDW (Rank) | NSC # | Mol. Formula | Mol. Weight | Energy Score | Vdw Score | ES Score | Structure |
|---|---|---|---|---|---|---|---|
| ES1 | 112322 | $C_{19}H_{21}N_3O_6S$ | 419 | −31.559767 | −20.3767 | −11.183 | 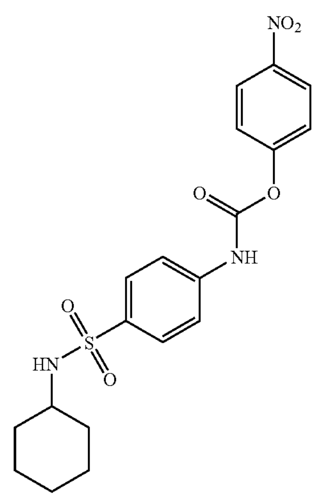 [SMILES: O=C(Nc1ccc(S(=O)(=O)NC2CCCCC2)cc1)Oc1ccc([N+](=O)[O-])cc1] |

TABLE 2-continued

| VDW (Rank) | NSC # | Mol. Formula | Mol. Weight | Energy Score | Vdw Score | ES Score | Structure |
|---|---|---|---|---|---|---|---|
| ES10 | 128948 | $C_{19}H_{13}Cl_2FN_2O_3S$ | 439 | −27.63699 | −21.8421 | −5.7949 | 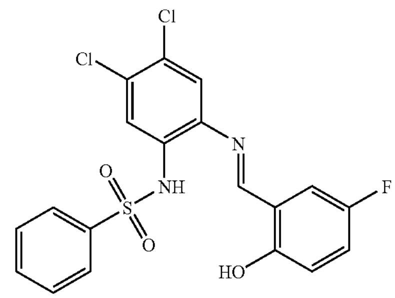 [SMILES: O=S(=O)(Nc1cc(Cl)c(Cl)cc1/N=C/c1cc(F)ccc1O)c1ccccc1] |
| ES17 | 128946 | $C_{19}H_{13}BrCl_2N_2O_3S$ | 500 | −26.394958 | −22.3986 | −3.9963 | 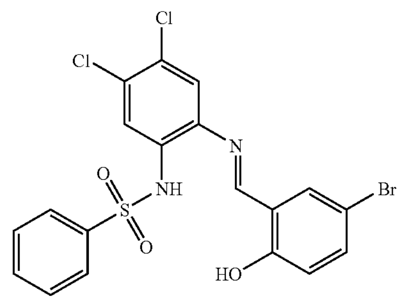 [SMILES: O=S(=O)(Nc1cc(Cl)c(Cl)cc1/N=C/c1cc(Br)ccc1O)c1ccccc1] |
| 3 | 45095 | $C_{12}H_5Cl_3N_2O_5$ | 364 | −21.731833 | −22.9213 | 1.18943 | 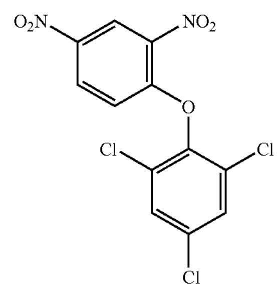 [SMILES: O=[N+]([O-])c1ccc(Oc2c(Cl)cc(Cl)cc2Cl)c([N+](=O)[O-])c1] |
| 4 | 93776 | $C_{12}H_9ClN_2O_4S$ | 313 | −22.875412 | −22.7232 | −0.1523 | 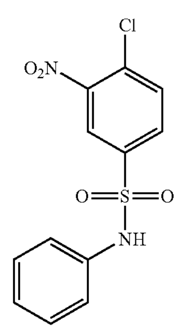 [SMILES: O=[N+]([O-])c1cc(S(=O)(=O)Nc2ccccc2)ccc1Cl] |
| 5 | 128945 | $C_{19}H_{13}Cl_3N_2O_3S$ | 456 | −27.179604 | −22.6513 | −4.5283 | 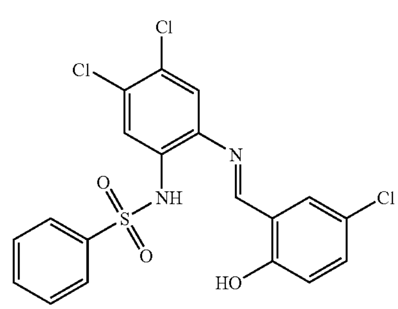 [SMILES: O=S(=O)(Nc1cc(Cl)c(Cl)cc1/N=C/c1cc(Cl)ccc1O)c1ccccc1] |

TABLE 2-continued

| VDW (Rank) | NSC # | Mol. Formula | Mol. Weight | Energy Score | Vdw Score | ES Score | Structure |
|---|---|---|---|---|---|---|---|
| 6 | 128946 | C$_{19}$H$_{13}$BrCl$_2$N$_2$O$_3$S | 500 | −26.394958 | −22.3986 | −3.9963 | 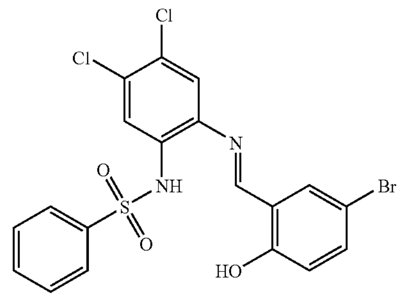 [SMILES: O=S(=O)(Nc1cc(Cl)c(Cl)cc1/N=C/c1cc(Br)ccc1O)c1ccccc1] |
| 9 | 626628 | C$_{15}$H$_{12}$Br$_2$N$_4$O$_3$ | 456 | −21.890352 | −22.0148 | 0.12446 | 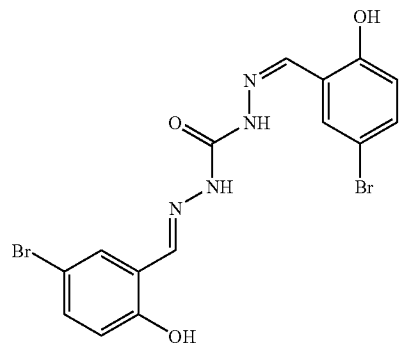 [SMILES: O=C(N/N=C\c1cc(Br)ccc1O)N/N=C/c1cc(Br)ccc1O] |
| 11 | 338583 | C$_{17}$H$_{16}$N$_2$O$_4$ | 312 | −25.357153 | −21.9484 | −3.4087 | 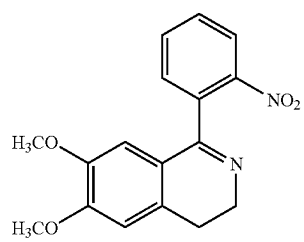 [SMILES: COc1cc2c(cc1OC)C(c1ccccc1[N+](=O)[O-])=NCC2] |
| 13 | 29422 | C$_{10}$H$_{13}$N$_5$O$_4$S | 299 | −18.105143 | −21.9225 | 3.81736 | 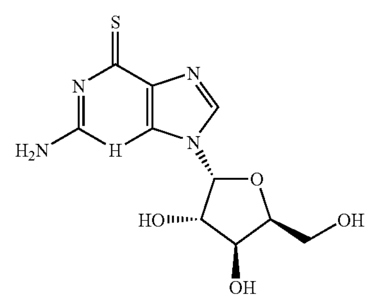 |

As shown herein, these compounds have antiproliferative activity; without wishing to be bound by theory, it is believed that the compounds mimic p27 action by binding to the p27 binding site to inhibit cyclin-dependent kinase activity.

Example 5

Compounds of the Invention Inhibit Breast and Prostate Cancer Cell Proliferation Labeled thymidine ($^3$H-thymidine) incorporation assays were used to screen compounds at a concentration of 100 µM using mouse mammary epithelial cells and the human prostate cancer cell line DU145.

Human prostate cancer DU145 cells were plated at 30,000 cells per well in 24-well plates and allowed to attach for 24 hours. The cells were treated for 24 hours with either 100 µM of the indicated compounds, 0.1% DMSO as a vehicle control, or left untreated. The cells were pulsed with $^3$H-thymidine for two hours. The cells were fixed in 10% trichloroacetic acid and washed a total of three times with 10% trichloroacetic acid. The $^3$H-thymidine-labeled DNA was dissolved in 0.2% NaOH, mixed with scintillation fluid, and the associated radioactivity quantitated using a scintillation counter. These experiments were performed in triplicate and the results are presented as the average thymidine incorporation±standard deviation.

Seven of the molecules identified in Example 1 as having the top estimated binding energies (Hits/Compounds 3, 4, 6, 7, 8, 9, and 10) were obtained and tested for their ability to induce cell cycle arrest of mouse mammary NMuMG and DU145 human prostatic carcinoma cell lines in $^3$H-thymidine incorporation assays (FIG. 2C). Although hit #2 was unavailable, it was shown in an NCI screen to inhibit the proliferation of multiple human cancer cell lines with an average 50% inhibitory concentration ($IC_{50}$) of 12 µM. Thus at least five of the ten top-ranked compounds are cell permeable and induce an appreciable arrest of cancer cell proliferation. Of the four compounds tested in our laboratory that inhibited cell proliferation (3, 4, 7, and 10), Hit #10 was unique in inducing a dramatic morphological change in a fraction of both the NMuMG and DU145 cells (FIG. 2D).

FIG. 2 shows that Compounds 3, 4, 7 and 10 significantly inhibited proliferation and prompted biochemical evaluation of the targeted proteins in the treated cells.

Figure 4:
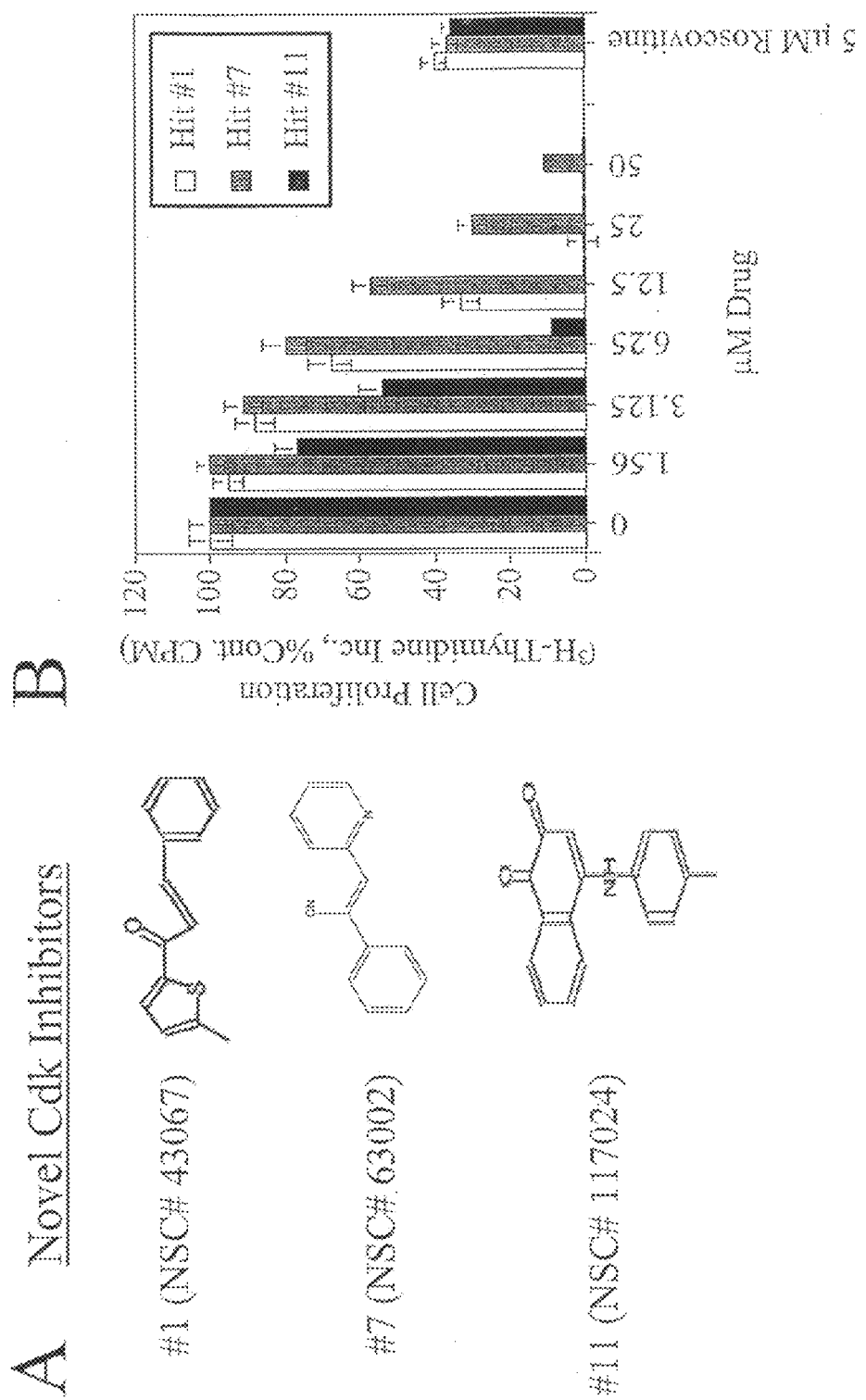
FIG. 4. Compounds #1, #7, and #11 inhibit proliferation of BT549 breast cancer cells. BT549 cells were treated for 24 hours with the indicated "Pocket #1" compounds. The effect of treatment on cell proliferation was quantitated by measuring the amount of $^{3}$H-Thymidine incorporated into cellular DNA over a two hour time interval. The results are presented as the average of triplicate determinations ±standard deviation.

Similarly, FIG. 4 shows that Compounds 1, 7 and 11 inhibit the proliferation of BT549 breast cancer cells in vitro. Both compounds are more potent than Compound 7 in this assay, with Compound 1 being effective at low micromolar concentrations and Compound 11 effective at high nanomolar to low micromolar concentrations. Moreover, there appears to be a preferential inhibition of cancer cells over nontransformed cells with Compound 11 (data not shown).

Figure 5:
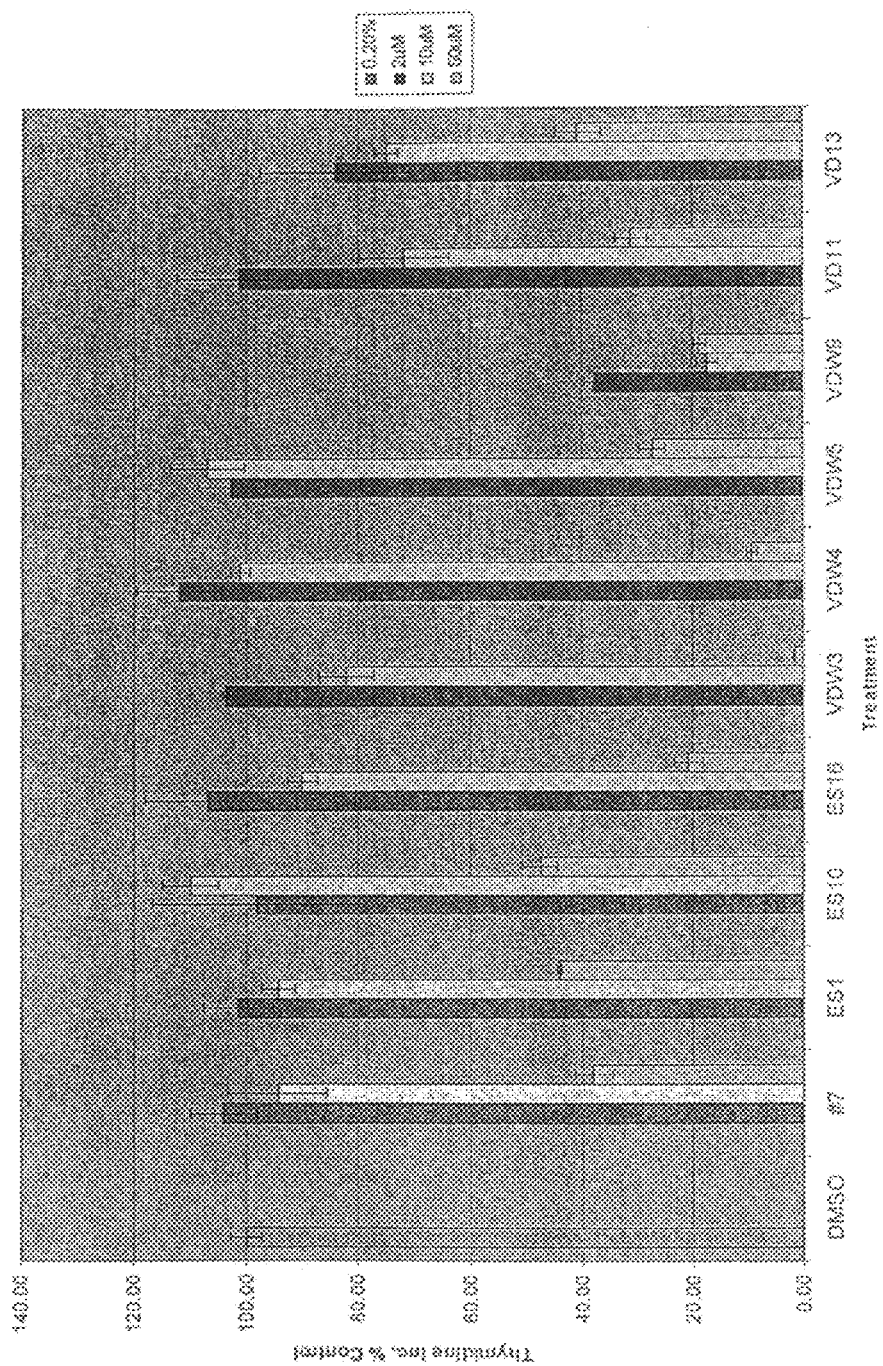
FIG. 5. Compounds predicted to bind to "Pocket #2" inhibit proliferation of BT549 breast cancer cells. BT549 cells were treated for 24 hours with the indicated "Pocket #2" compounds. The effect of treatment on cell proliferation was quantitated by measuring the amount of $^{3}$H-Thymidine incorporated into cellular DNA over a two hour time interval. The results are presented as the average of triplicate determinations ±standard deviation.

Additional $^3$H-thymidine incorporation assays were performed to determine whether the "Pocket #2" binding drugs (see Table 2) inhibit cell proliferation at concentrations lower than 100 µM. These experiments (shown in FIG. 5) indicated that all of the compounds inhibit proliferation significantly at 50 µM; the "Pocket #2" compound designated as VDW9 inhibited proliferation at both 10 µM and 2 µM.

Example 6

Figure 7:
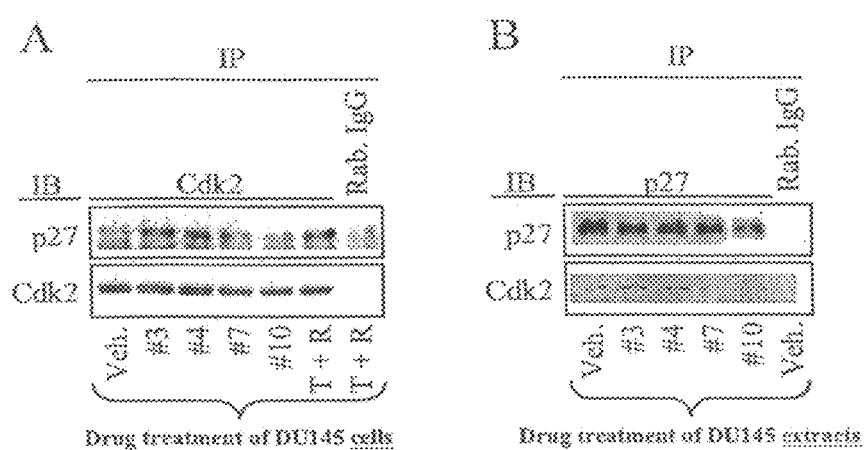
FIG. 7. Compounds (Hits) #3 and #4 increase p27 binding to Cdk2. (A) DU145 cells were treated for 24 h with 100 μM of the indicated compounds, 0.2% DMSO as a vehicle control (Veh.), or TGFβ+rapamycin (T+R) as a positive control for the induction of p27 binding to Cdk2. Cell extracts were immunoprecipitated with antibodies to Cdk2, and the immunoprecipitates blotted for p27 or Cdk2. (B) The indicated compounds were added to identical aliquots of DU145 cell extract to a final concentration of 100 μM and the treated extracts subjected to immunoprecipitation with p27 antibodies. Immunoprecipitates were immunoblotted with p27 or Cdk2 antibodies.

4-Tert-Butyl-2-Nitroaniline Decreases the Intracellular Levels of Cdk2 and P27 Complexes Western blot analysis demonstrated increased association of p27 with Cdk2 in cancer lines treated with 4-tert-Butyl-2-nitroaniline. FIG. 7 is a representative Western blot which demonstrates that 4-tert-Butyl-2-nitroaniline (Compound 3) is selective for a family of related Cdk and Cyclin kinases. Induction of p27/p21 binding to Cdks by a compound is believed to be predictive of the ability of the compound to inhibit Cdks in kinase assays, and to inhibit cell proliferation in $^3$H-thymidine incorporation assays.

Figure 6:
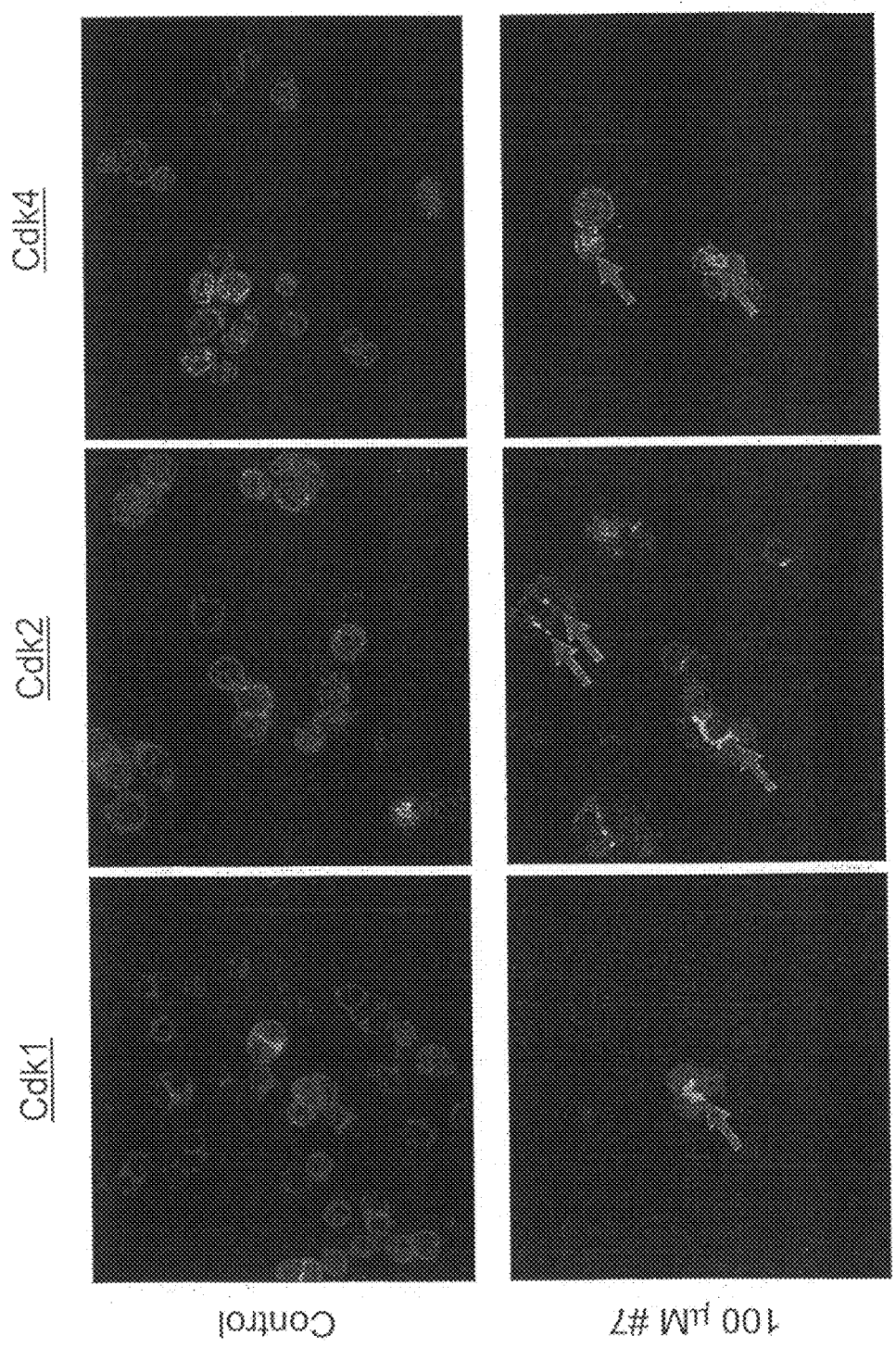
FIG. 6. Immunofluorescence microscopy of cellular distribution of Cdks in the absence (upper panels) and presence (lower panels) of a compound of the invention. MDA-MB-468 breast cancer cells were treated with the indicated concentration of pocket 1 compound #7 for 24 hours. Immunofluorescence microscopy was performed using an antibody to Cdk2. The results indicate that Compound #7 causes a change in Cdk2 localization consistent with aggregation. These aggregates are most apparent at sites of cell-cell contact.

It appears that compounds of the invention can cause redistribution of Cdk1, Cdk2, and Cdk4 in cells. As shown in FIG. 6, immunofluorescence microscopy experiments indicate that drug #7 causes from a uniform distribution in the cytoplasm (lightest color), to a localization consistent with aggregation (indicated by arrows). For Cdk1 and Cdk2 these aggregates appear primarily at cell-cell junctions. For Cdk4 these aggregates appear on top of the nuclei.

Example 7

Figure 8:
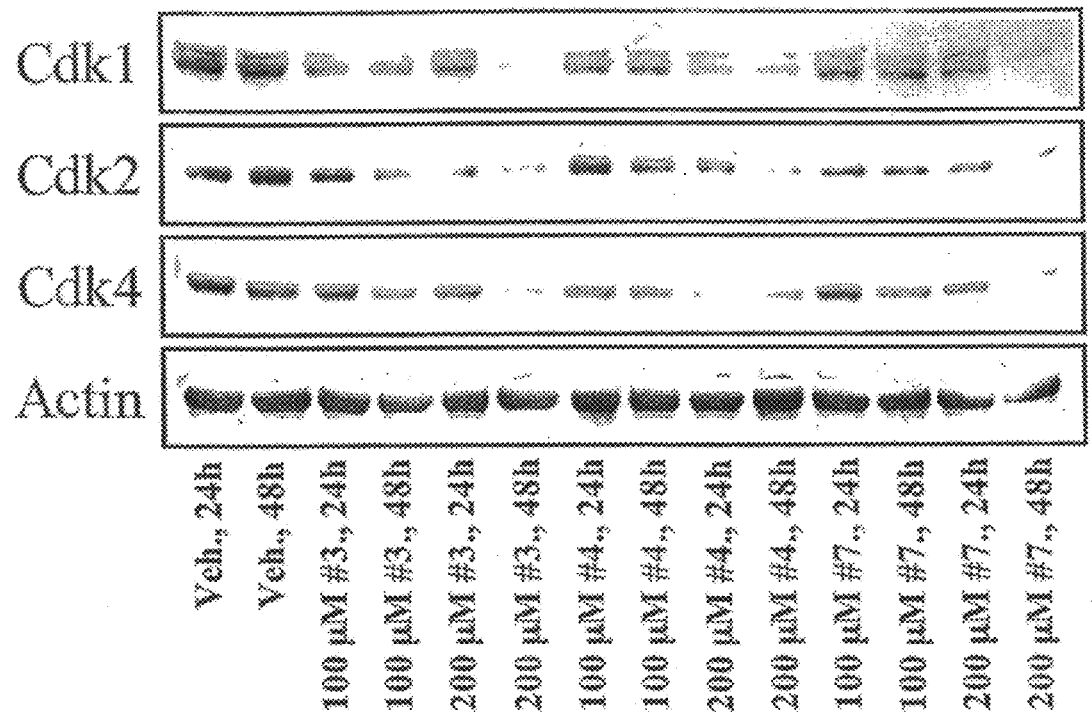
FIG. 8 is a Western blot showing that compounds of the invention decrease the cellular levels of Cdk1, Cdk2, and Cdk4 in a time- and dose-dependent manner. BT549 cells were treated with the indicated Pocket #1 compounds for the indicated intervals. Cell lysates were prepared and the amounts of Cdk1, Cdk2, and Cdk4 were determined by immunoblot. Actin staining serves as a loading control. DMSO serves as a vehicle control.

Compounds 3, 4, and 7 Decrease the Cellular Levels of Cdk1, Cdk2, and Cdk4 in a Time- and Dose-Dependent Manner As shown in FIG. 8, compounds of the invention can decrease cellular levels of Cdks. Human breast cancer BT549 cells were treated as indicated for 24 or 48 hours with either 0.2% DMSO as a vehicle control, or compounds #3, #4, and #7 at the indicated concentrations. Cell lysates were prepared, normalized for protein content, resolved by SDS-PAGE and the proteins transferred to nitrocellulose. Levels of Cdk1, Cdk2, and Cdk4 were measured using primary antibodies specific for these proteins, followed by alkaline-phosphatase-conjugated secondary antibodies and colorimetric detection using the substrate NBT/BCIP. Actin is used as a control to demonstrate equal protein loading.

Example 8

4-Tert-Butyl-2-Nitroaniline Inhibits Tumor Invasiveness In Vitro

A cell invasion assay was performed on an aggressive prostate cancer cell line, Gs-α, to determine the effects of selected compounds that inhibit cell proliferation.

The experiment was performed in six-well Matrigel two-tier invasion chambers (Collaborative Biomedical Products, Bedford, Mass., USA), using a protocol similar to that used successfully by others (see, e.g., Chien J, Wong E, Nikes E et al., *Oncogene* 1999; 18: 3376-3382, incorporated herein by reference). Prostate cancer cells ($2.5 \times 10^5$ cells per well expressing hairpin double-stranded CD44v interfering RNA or controls) were seeded in the upper insert in a serum-free basal medium (RPMI 1640 medium containing 0.1% BSA, 150 mg/ml of G418, 4 mM L-glutamine, 100 µg/ml penicillin G and 100 µg/ml streptomycin). The lower chamber contained chemoattractant medium consisting of 70% complete medium, 10% fetal bovine serum, and 20% conditioned medium obtained from subconfluent cultures. The incubations were carried out for 36 h. After this period, upper inserts were removed, and residual cells were removed from the upper Matrigel surface using cotton swabs. The invasive cells would penetrate through the Matrigel layer and would be on the outside bottom of the upper insert.

While the membranes were still wet in culture dishes, the GFP-positive cells on the entire membrane were counted under fluorescent illumination. Gels were fixed, stained using Diff Quik staining (Dade Diagnostic, Aguar, PR, USA), and mounted on glass slides. The total number of cells on the entire gel was counted. The data from invasion assay were corrected for cell growth during experimental periods as follows: the experimental cells were plated at a density of $10^5$ cells per well in six-well control inserts in chemoattractant medium and increase in cell number were determined after 48 h. Four experiments were carried out with PC3M cells and five with $G_s\alpha$ cells. The results were expressed as mean±standard deviation.

The "Percent Invasion" is defined as: 100×(Number of cells invading through entire Matrigel insert membrane)/Number of cells invading through entire control insert membrane.

The "Invasion Index" is defined as: 100×(Percent Invasion of treated cells)/(Percent Invasion of untreated cells).

Significance of differences in Percent Invasion according to treatment (or transfection of Metafectene vehicle alone) were assessed by Student's t-test.

Figure 9:
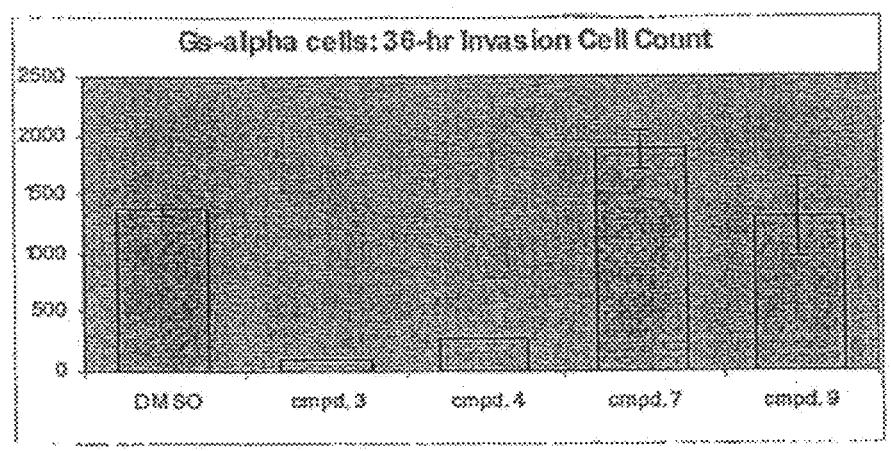
FIG. 9. In vitro invasiveness assays demonstrate that 4-tert-Butyl-2-nitroaniline significantly inhibits tumor invasiveness in a highly invasive prostate tumor cell line.

As shown in FIG. 9, 4-tert-Butyl-2-nitroaniline significantly inhibits cell invasiveness in vitro. Compound 1 was also found to inhibit cell invasiveness (data not shown).

Example 9

Intratumor Injections of 4-Tert-Butyl-2-Nitroaniline Reduce Tumor Size In Vivo in Combination with CD44 RNA Interference Previous studies have suggested that CD44 RNA interference influences the kinetics and invasiveness of prostate cancer cells PC-3. The effect of 4-tert-Butyl-2-nitroaniline when combined with CD44 RNA interference was therefore investigated.

Seven-wk-old mice (Jackson Laboratory, Bar Harbor, Me.) were injected in the right flank with $2 \times 10^6$ PC-3 tumor cells in 500 µl liquid Matrigel. Metafectene (Biontex, Munich, Germany), shown to facilitate superior transfection (Iczkowski K A, Omara-Opyene A L, and Klösel R., *Molecular Biotechnology* 2004; 28:97-103), was used for transfection. By 14 days after injection, a tumor mass was palpable and at 27 days, 4-tert-Butyl-2-nitroaniline and CD44 RNAi therapy commenced. Gene transfection was controlled for quantitation by injecting a constant 10 µg of vector. This approach involved mixing volume of DNA containing 10 µg of pU6BS (and subsequently pTracer) plasmid having the CD44 RNAi construct with 10 µl of Metafectene before injection into the tumor. Both Metafectene and DNA were diluted separately in 100 µl of sterile serum-free RPMI before mixing (see, e.g., Iczkowski K A, Omara-Opyene A L, and Klösel R., *Molecular Biotechnology* 2004; 28:97-103). The mixture was then allowed to stand for 30 minutes before injection to allow the formation of Metafectene:DNA complexes.

Intra-tumoral injection was performed five times weekly, angling the needle at different areas of the tumor during a given injection as well as varying the injection site for each injection occasion. Control animals were injected with 100 µl consisting of 50 µl empty vector/medium plus 50 µl of Metafectene.

Figure 10:
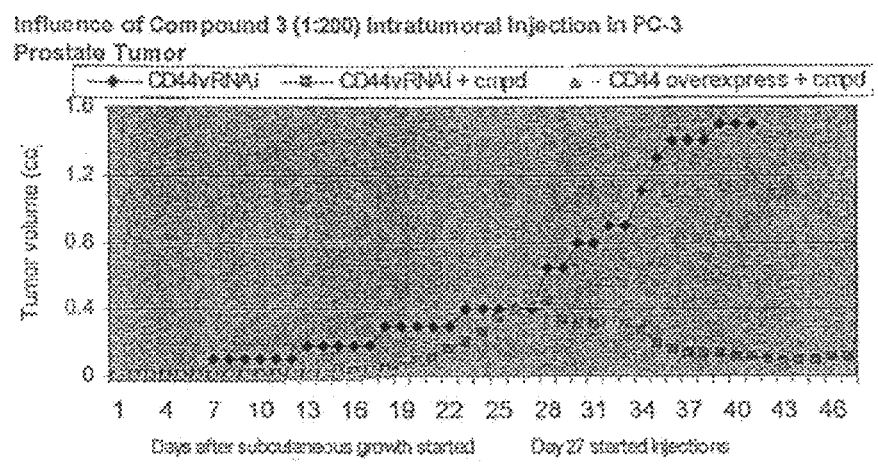
FIG. 10. In vivo activity of 4-tert-Butyl-2-nitroaniline in shrinking a highly aggressive prostate cancer cell line, PC-3, in combination with CD44 RNA interference.

As shown in FIG. 10, 4-tert-Butyl-2-nitroaniline had a significant effect on shrinking the tumor volume when combined with CD44 RNA interference. After 11 days of injection, tumor volume had decreased more than 50% in three treated animals but not in controls, ruling out the possibility that the vehicle alone could alter tumor size.

Example 10

Compounds of the Invention Inhibit Tumor Growth in a Mouse Xenograft Tumor Model A compound of the invention (Compound 1) was tested in a mouse xenograft tumor model to determine whether the compound can inhibit tumor growth in vivo.

SCID mice were subcutaneously implanted with PC3 prostate tumor cells in the flank and were administered intratumorally with controls (DMSO) or a test compound.

The two control animals were sacrificed when the total tumor volume (L×W×H) exceeded 1.5 cc. The treated animal was sacrificed because a small but significant skin ulceration was developing over the tumor.

It was found that Compound 1 injections markedly reduced tumor growth in the treated animal at 1:50 dilution (2 mM) compared with 1:50 DMSO in PBS in two controls.

REFERENCES

1. *Cancer Facts and Figures* 2005. 2005, Atlanta: American Cancer Society; 2005.
2. Kalkhoven, E., et al., Resistance to transforming growth factor beta and activin due to reduced receptor expression in human breast tumor cell lines. *Cell Growth Differ,* 1995. 6(9): p. 1151-61.
3. Bottinger, E. P., et al., Transgenic mice overexpressing a dominant-negative mutant type II transforming growth factor beta receptor show enhanced tumorigenesis in the mammary gland and lung in response to the carcinogen 7,12-dimethylbenz-[a]-anthracene. *Cancer Res,* 1997. 57(24): p. 5564-70.
4. Chen, C. R., Y. Kang, and J. Massague, Defective repression of c-myc in breast cancer cells: A loss at the core of the transforming growth factor beta growth arrest program. *Proc Natl Acad Sci USA,* 2001. 98(3): p. 992-9.
5. Grewe, M., et al., Regulation of cell growth and cyclin D1 expression by the constitutively active FRAP-p70s6K pathway in human pancreatic cancer cells. *Cancer Res,* 1999. 59(15): p. 3581-7.
6. Seufferlein, T. and E. Rozengurt, Rapamycin inhibits constitutive p70s6k phosphorylation, cell proliferation, and colony formation in small cell lung cancer cells. *Cancer Res,* 1996. 56(17): p. 3895-7.
7. Law, B. K., et al., Rapamycin potentiates transforming growth factor beta-induced growth arrest in nontransformed, oncogene-transformed, and human cancer cells. *Mol Cell Biol,* 2002. 22(23): p. 8184-98.
8. Brown, K. A., et al., Transforming growth factor-beta induces Cdk2 relocalization to the cytoplasm coincident with dephosphorylation of retinoblastoma tumor suppressor protein. *Breast Cancer Res,* 2004. 6(2): p. R130-R139.
9. Ueki, N., et al., Potentiation of metastatic capacity by transforming growth factor-beta 1 gene transfection. *Jpn J Cancer Res,* 1993. 84(6): p. 589-93.
10. McEarchern, J. A., et al., Invasion and metastasis of a mammary tumor involves TGF-beta signaling. *Int J Cancer,* 2001. 91(1): p. 76-82.
11. Muraoka, R. S., et al., Blockade of TGF-beta inhibits mammary tumor cell viability, migration, and metastases. *J Clin Invest,* 2002. 109(12): p. 1551-9.
12. Roberts, A. B., et al., Is Smad3 a major player in signal transduction pathways leading to fibrogenesis? *Chest,* 2001. 120(1 Suppl): p. 43S-47S.
13. Sandberg, E. M., et al., Identification of 1,2,3,4,5,6-hexabromocyclohexane as a small molecule inhibitor of jak2 tyrosine kinase autophosphorylation [correction of autophosphorylation]. *J Med Chem,* 2005. 48(7): p. 2526-33.
14. Huentelman, M. J., et al., Structure-based discovery of a novel angiotensin-converting enzyme 2 inhibitor. *Hypertension,* 2004. 44(6): p. 903-6.
15. Peng, H., et al., Identification of novel inhibitors of BCR-ABL tyrosine kinase via virtual screening. *Bioorg Med Chem Lett,* 2003. 13(21): p. 3693-9.
16. Enyedy, I. J., et al., Discovery of small-molecule inhibitors of Bcl-2 through structure-based computer screening. *J Med Chem,* 2001. 44(25): p. 4313-24.
17. Jeffrey, P. D., et al., Mechanism of CDK activation revealed by the structure of a cyclinA-CDK2 complex. *Nature,* 1995. 376(6538): p. 313-20.
18. Russo, A. A., et al., Crystal structure of the p27Kip1 cyclin-dependent-kinase inhibitor bound to the cyclin A-Cdk2 complex. *Nature,* 1996. 382(6589): p. 325-31.
19. Charifson, P. S., et al., Consensus scoring: A method for obtaining improved hit rates from docking databases of three-dimensional structures into proteins. *J Med Chem,* 1999. 42(25): p. 5100-9.
20. Ewing, T. J., et al., DOCK 4.0: search strategies for automated molecular docking of flexible molecule databases. *J Comput Aided Mol Des,* 2001. 15(5): p. 411-28.
21. Bayart, E., et al., A major role for mitotic CDC2 kinase inactivation in the establishment of the mitotic DNA damage checkpoint. *Cancer Res,* 2004. 64(24): p. 8954-9.

22. Nakayama, K., et al., Skp2-mediated degradation of p27 regulates progression into mitosis. *Dev Cell*, 2004. 6(5): p. 661-72.
23. Pagano, M., Control of DNA synthesis and mitosis by the Skp2-p27-Cdk1/2 axis. *Mol Cell*, 2004. 14(4): p. 414-6.
24. Chytil, A., et al., Construction of a cyclin D1-cdk2 fusion protein to model the biological functions of cyclin D1-cdk2 complexes. *J Biol Chem*, 2004. 279(46): p. 47688-98.
25. Tetsu, O. and F. McCormick, Proliferation of cancer cells despite CDK2 inhibition. *Cancer Cell*, 2003. 3(3): p. 233-45.
26. Monga, M. and E. A. Sausville, Developmental therapeutics program at the NCI: molecular target and drug discovery process. *Leukemia*, 2002. 16(4): p. 520-6.
27. Irwin, J. J. and B. K. Shoichet, ZINC—a free database of commercially available compounds for virtual screening. *J Chem Inf Model*, 2005. 45(1): p. 177-82.
28. Gschwend, D. A. and I. D. Kuntz, Orientational sampling and rigid-body minimization in molecular docking revisited: on-the-fly optimization and degeneracy removal. *J Comput Aided Mol Des*, 1996. 10(2): p. 123-32.
29. Good, A. C., et al., New molecular shape descriptors: application in database screening. *J Comput Aided Mol Des*, 1995. 9(1): p. 1-12.
30. Guex, N., A. Diemand, and M. C. Peitsch, Protein modelling for all. *Trends Biochem Sci*, 1999. 24(9): p. 364-7.
31. Guex, N. and M. C. Peitsch, SWISS-MODEL and the Swiss-Pdb Viewer: an environment for comparative protein modeling. *Electrophoresis*, 1997. 18(15): p. 2714-23.
32. Zhang, J. and T. L. Madden, PowerBLAST: a new network BLAST application for interactive or automated sequence analysis and annotation. *Genome Res*, 1997. 7(6): p. 649-56.
33. Peitsch, M. C., T. Schwede, and N. Guex, Automated protein modelling—the proteome in 3D. *Pharmacogenomics*, 2000. 1(3): p. 257-66.
34. Peitsch, M. C., ProMod and Swiss-Model: Internet-based tools for automated comparative protein modelling. *Biochem Soc Trans*, 1996. 24(1): p. 274-9.
35. van Gunsteren, W. F., *Biomolecular simulation: The GROMOS96 manual and user guide*. 1996.
36. Collaborative Computational Project, N., The CCP4 Suite: Programs for Protein Crystallography. *ACTA Cryst.*, 1994. D50: p. 760-763.
37. Datto, M. B., Y. Yu, and X. F. Wang, Functional analysis of the transforming growth factor beta responsive elements in the WAF1/Cip1/p21 promoter. *J Biol Chem*, 1995. 270 (48): p. 28623-8.
38. Florenes, V. A., et al., TGF-beta mediated G1 arrest in a human melanoma cell line lacking p15INK4B: evidence for cooperation between p21Cip1/WAF1 and p27Kip1. *Oncogene*, 1996. 13(11): p. 2447-57.
39. Berthet, C., et al., Cdk2 knockout mice are viable. *Curr Biol*, 2003. 13(20): p. 1775-85.
40. Ortega, S., et al., Cyclin-dependent kinase 2 is essential for meiosis but not for mitotic cell division in mice. *Nat Genet*, 2003. 35(1): p. 25-31.
41. Malumbres, M., et al., Mammalian cells cycle without the D-type cyclin-dependent kinases Cdk4 and Cdk6. *Cell*, 2004. 118(4): p. 493-504.
42. Kozar, K., et al., Mouse development and cell proliferation in the absence of D-cyclins. *Cell*, 2004. 118(4): p. 477-91.

The disclosures of each and every patent, patent application and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A method of treating a subject suffering from breast cancer or prostate cancer, the method comprising administering to subject in need thereof a therapeutically effective amount of a compound capable of stabilizing the interaction of a cyclin-dependent kinase and a cdk inhibitor, or a compound capable of stabilizing an inactive conformation of a cyclin-dependent kinase and/or a complex of a cyclin-dependent kinase and a cyclin, such that the subject is treated wherein the compound is selected from the group consisting of 1-(5-methyl-thiophen-2-yl)-3-phenyl-propenone, 4-t-butyl-2-nitro-aniline, 3-amino-1-sulfanylidene-5,6,7,8-tetrahydroisothiochromene-4-carbonitrile, and 4-p-tolylamino-[1,2]naphthoquinone".

2. The method of claim 1, wherein the cdk inhibitor is p27.

3. The method of claim 2, wherein the compound is selected from

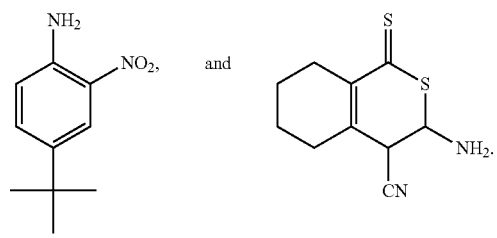

and

4. The method of claim 1, wherein the cancer is breast cancer and the compound is 1-(5-methyl-thiophen-2-yl)-3-phenyl-propenone.

5. A method for inhibiting breast cancer or prostate cancer cell proliferation, comprising contacting a breast cancer cell or a prostate cancer cell with a compound capable of stabilizing an interaction between a cyclin dependent kinase and p27, such that cancer cell proliferation is inhibited wherein the compound is selected from the group consisting of 1-(5-methyl-thiophen-2-yl)-3-phenyl-propenone, 4-t-butyl-2-nitro-aniline, 3-amino-1-sulfanylidene-5,6,7,8-tetrahydroisothiochromene-4-carbonitrile, and 4-p-tolylamino-[1,2]naphthoquinone".

6. The method of claim 5, wherein the cell is a breast cancer cell and the compound is 1-(5-methyl-thiophen-2-yl)-3-phenyl-propenone.

7. A method of treating a subject suffering from breast cancer or prostate cancer, the method comprising administering to subject in need thereof a therapeutically effective amount of a compound selected from the group consisting of 1-(5-methyl-thiophen-2-yl)-3-phenyl-propenone, 4-t-butyl-2-nitro-aniline, 3-amino-1-sulfanylidene-5,6,7,8-tetrahydroisothiochromene-4-carbonitrile, and 4-p-tolylamino-[1,2]naphthoquinone, such that the subject is treated.

8. A method for inhibiting breast cancer or prostate cancer cell proliferation, comprising contacting a breast cancer cell or a prostate cell with a compound selected from the group consisting of 1-(5-methyl-thiophen-2-yl)-3-phenyl-propenone, 4-t-butyl-2-nitro-aniline, 3-amino-1-sulfanylidene-5,6,7,8-tetrahydroisothiochromene-4-carbonitrile, and 4-p-tolylamino-[1,2]naphthoquinone, such that breast cancer or prostate cancer cell proliferation is inhibited.

* * * * *